(12) United States Patent  
Yamamoto

(10) Patent No.: US 8,129,990 B2
(45) Date of Patent: Mar. 6, 2012

(54) IMAGE PROCESSING APPARATUS AND COMPUTER PROGRAM PRODUCT

(75) Inventor: Yoko Yamamoto, Hachioji (JP)

(73) Assignee: Olympus Corporation, Tokyo (JP)

( * ) Notice: Subject to any disclaimer, the term of this patent is extended or adjusted under 35 U.S.C. 154(b) by 615 days.

(21) Appl. No.: 12/329,765

(22) Filed: Dec. 8, 2008

(65) Prior Publication Data

US 2009/0141960 A1 Jun. 4, 2009

Related U.S. Application Data

(63) Continuation of application No. PCT/JP2007/060643, filed on May 24, 2007.

(30) Foreign Application Priority Data

Jun. 7, 2006 (JP) .................................. 2006-158984

(51) Int. Cl.
 *G01V 3/00* (2006.01)

(52) U.S. Cl. ........................................ 324/300; 324/309

(58) Field of Classification Search .......... 324/300–322; 600/400–555; 382/133, 103; 348/135, 137; 377/10, 11, 12
See application file for complete search history.

(56) References Cited

U.S. PATENT DOCUMENTS

| | | | | |
|---|---|---|---|---|
| 5,029,919 A * | 7/1991 | Bauer | ........................... | 293/134 |
| 5,031,099 A * | 7/1991 | Kettler | ........................... | 382/133 |
| 8,019,143 B2 * | 9/2011 | Kanda | ........................... | 382/133 |
| 2004/0128077 A1 | 7/2004 | Koebler et al. | | |
| 2006/0008843 A1 * | 1/2006 | Sachesenmeier et al. | ..... | 435/7.1 |
| 2006/0098858 A1 | 5/2006 | Guittet | | |
| 2006/0194307 A1 * | 8/2006 | Yasuda et al. | .............. | 435/288.7 |

FOREIGN PATENT DOCUMENTS

| | | |
|---|---|---|
| JP | 2-171866 | 7/1990 |
| JP | 7-75554 | 3/1995 |
| JP | 8-136536 | 5/1996 |
| JP | 11-32325 A | 2/1999 |
| JP | 2001-500744 | 1/2001 |
| JP | 2006-506635 | 2/2006 |
| JP | 2006-350740 | 12/2006 |
| WO | WO 97/19834 | 6/1997 |

OTHER PUBLICATIONS

Japanese Office Action dated Nov. 1, 2011 from corresponding Japanese Patent Application No. 2006-158984 together with partial English language translation.

* cited by examiner

*Primary Examiner* — Brij Shrivastav
(74) *Attorney, Agent, or Firm* — Scully, Scott, Murphy & Presser, P.C.

(57) ABSTRACT

An image processing apparatus includes a recognition unit that recognizes each cell area corresponding to a living cell from a series of observation images captured at observation time points; a measurement unit that measures cell characteristic amounts of each cell; a tracking unit that determines whether a cell area captured at a processing target time point and a cell area captured earlier than the processing target time point has an identity with each other, and associates the cell areas which have an identity with each other; and a cell division detection processing unit that measures relative position information between a target cell area to be processed and a peripheral cell area positioned around the target cell area, determines whether cell division has occurred in a living cell based on at least the relative position information, and detects a target cell area on which cell division has occurred.

14 Claims, 17 Drawing Sheets

FIG.5

| -1 | -1 | -1 |
|----|----|----|
| -1 | 9  | -1 |
| -1 | -1 | -1 |

OBSERVATION TIME POINT $t_p$

OBSERVATION TIME POINT $t_q$

IMAGE PROCESSING APPARATUS AND COMPUTER PROGRAM PRODUCT

CROSS-REFERENCE TO RELATED APPLICATIONS

This application is a continuation of PCT international application Ser. No. PCT/JP2007/060643 filed on May 24, 2007 which designates the United States, incorporated herein by reference, and which claims the benefit of priority from Japanese Patent Application No. 2006-158984, filed on Jun. 7, 2006, incorporated herein by reference.

BACKGROUND OF THE INVENTION

1. Field of the Invention

The present invention relates to an image processing apparatus that processes observation images in which a cell is recorded, and a computer program product thereof.

2. Description of the Related Art

In a cell, genetic information doubles because of DNA replication, and doubled genetic information is allocated to two daughter cells by cell division, which achieves continuous growth white maintaining certain genetic information. When appropriate conditions for growth (growth factor), including rich nutrition, is satisfied, the cell cycle progresses, and if the DNA is damaged due to application of a radiation ray or an ultraviolet ray (DNA damages), the progress stops. The progress of the cell cycle is usually strictly controlled based on factors of, for example, whether DAN damage occurs and whether there is a growth factor. It is considered that the normal control is essential for life. It is said that failure in the cell cycle out of the normal control deeply relates to the process of canceration.

With recently increasing importance of study on the cell cycle, study on the cell cycle, control mechanism, and preventing method has been progressed to find out the mechanism of cancer and develop medical drugs.

Particularly, to find out the cancer mechanism and specify targets of drug discovery, understanding the cell state in the cell cycle is important. Particularly, understanding the phenomenon that a cell divides and grows is important, and there is a demand for accurately detecting cell division. To detect cell division, various kinds of methods have been developed.

Japanese Patent Application Laid-open No. 7-75554 discloses a method of evaluating the growth state using an image in which cells are recorded (hereinafter, referred to as "cell image"). In this method, the size of each cell is obtained by image processing, and the average of the obtained sizes is used as an index representing the level of growth, which makes it possible to statistically evaluate the cell growth state.

Published Japanese Translation No. 2001-5007444 of the PCT International Publication discloses a method of evaluating the state of cell division using cell images. In the image processing in the method, whether it is a cell is determined by comparing the amount of cell characteristics, particularly, the shape characteristics including the area and circumference, with that of a model previously prepared based on the shape characteristics, and the number of cells is obtained. Because the number of cells increases by cell division, cell division can be detected by monitoring the number of cells. Alternatively, by comparing the tendency in the shape characteristics and position with known tendency, division can be detected.

In the method disclosed in US Patent Application Publication No. 2004/0128077 Specification, cell division is detected by calculating parameters of a cell by image processing and chronologically obtaining the parameters of the cell.

SUMMARY OF THE INVENTION

An image processing apparatus according to an aspect of the present invention processes a series of observation images captured at a plurality of time points, in which a living cell is chronologically recorded. The image processing apparatus includes a cell recognizing unit that recognizes cell image areas corresponding to the living cell from the series of observation images; a characteristic amount measuring unit that measures cell characteristic amounts that represent characteristics of each of the cell image areas; a cell tracking unit that determines whether a tracking target area captured at a processing target time point among the cell image areas has an identity with a cell image area captured at a time point earlier than the processing target time point among the cell image areas, and that adds a tracking index indicating the an identity to the tracking target area on which it is determined that the tracking target area has the an identity; and a cell division detecting unit that regards a cell image area to which the tracking index is added as a target cell area to be processed, measuring relative position information indicating a relative position relationship between the target cell area and a peripheral cell area positioned around the target cell area, determining whether cell division has occurred in the living cell represented by the target cell area based on at least the relative position information, and detecting the target cell area on which it is determined that cell division has occurred.

A computer program product according to another aspect of the present invention has a computer readable medium including programmed instructions for processing a series of observation images captured at a plurality of time points, in which a cell area is chronologically recorded. The instructions, when executed by a computer, cause the computer to perform: recognizing cell image areas corresponding to the living cell from the series of observation images; measuring cell characteristic amounts that represent characteristics of each of the cell image areas; determining whether a tracking target area captured at a processing target time point among the cell image areas has an identity with a cell image area captured at a time point earlier than the processing target time point among the cell image areas, and adding a tracking index indicating the an identity to the tracking target area on which it is determined that the tracking target area has the an identity; and regarding a cell image area to which the tracking index is added as a target cell area to be processed, measuring relative position information indicating a relative position relationship between the target cell and a peripheral cell area positioned around the target cell area, determining whether cell division has occurred in the living cell represented by the target cell area based on at least the relative position information, and detecting the target cell area on which it is determined that cell division has occurred.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 4-1 is a diagram for explaining a processing method of smoothing processing.

FIG. 4-2 is a diagram for explaining the processing method of smoothing processing.

FIG. 4-3 is a diagram for explaining the processing method of smoothing processing.

FIG. 4-4 is a diagram for explaining the processing method of smoothing processing.

FIG. 4-5 is a diagram for explaining the processing method of smoothing processing.

FIG. 4-6 is a diagram for explaining the processing method of smoothing processing.

FIG. 4-7 is a diagram for explaining the processing method of smoothing processing.

FIG. 4-8 is a diagram for explaining the processing method of smoothing processing.

FIG. 4-9 is a diagram for explaining the processing method of smoothing processing.

FIG. 5 is a diagram of a sharpening filter.

FIG. 6 is a flowchart of a process procedure of cell division detection processing.

FIG. 7 is a diagram exemplarily showing cell images representing a cell area in which cell division has occurred.

FIG. 8 is a graph of an example of chronological variations in a total luminance.

FIG. 9 is a diagram for explaining an area position condition.

FIG. 11-1 is a diagram for explaining processing for elliptic approximation on a cell area.

FIG. 11-2 is a diagram for explaining the processing for elliptic approximation on a cell area.

FIG. 11-3 is a diagram for explaining the processing for elliptic approximation on a cell area.

DETAILED DESCRIPTION OF THE PREFERRED EMBODIMENTS

Figure 1:
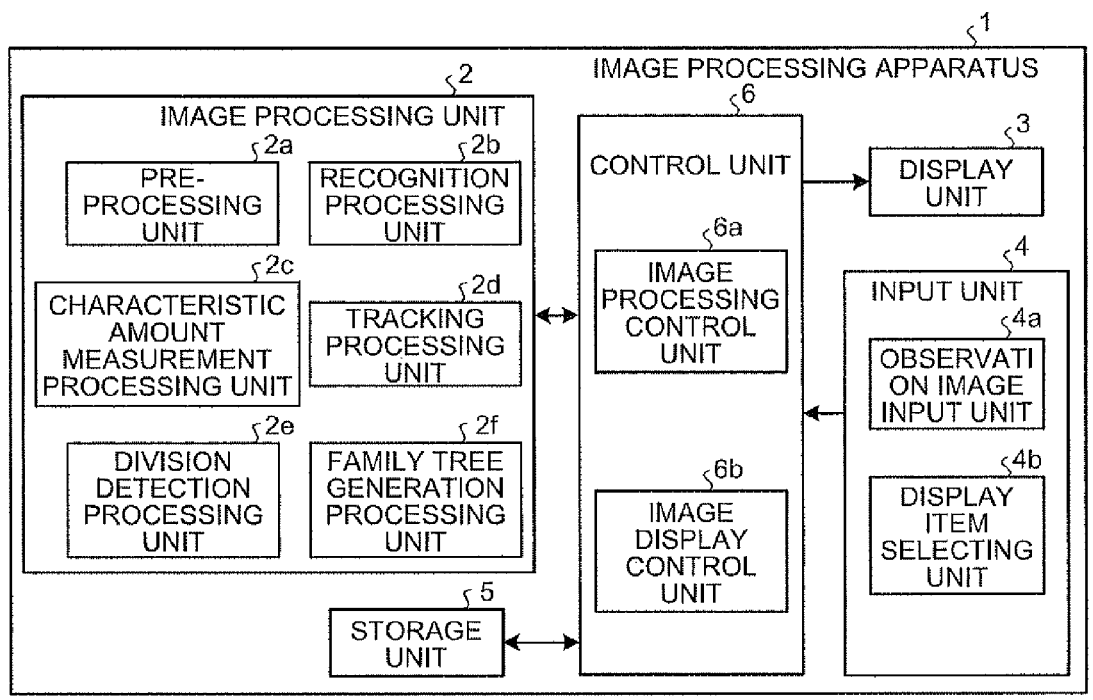
FIG. 1 is a block diagram of a configuration of an image processing apparatus according to a first embodiment of the present invention.

Preferred embodiments of an image processing apparatus and an image processing program according to the present invention are explained in detail below with reference to the accompanying drawings. The embodiments do not limit the present invention. The same constituents are denoted by the same reference numerals in the drawings.

First Embodiment

First, an image processing apparatus according to a first embodiment is explained. FIG. 1 is a block diagram of a relevant portion of an image processing apparatus 1 according to the first embodiment. As shown in FIG. 1, the image processing apparatus 1 includes an image processing unit 2 that process an image input thereto; a display unit 3 that displays various types of information; an input unit 4 that inputs various types of information; a storage unit 5 that stores therein various types of information; and a control unit 6 that controls processing and operations performed by the image processing apparatus 1. The image processing unit 2, the display unit 3, the input unit 4, and the storage unit 5 are electrically connected to the control unit 6 and controlled by the control unit 6.

Figure 2:
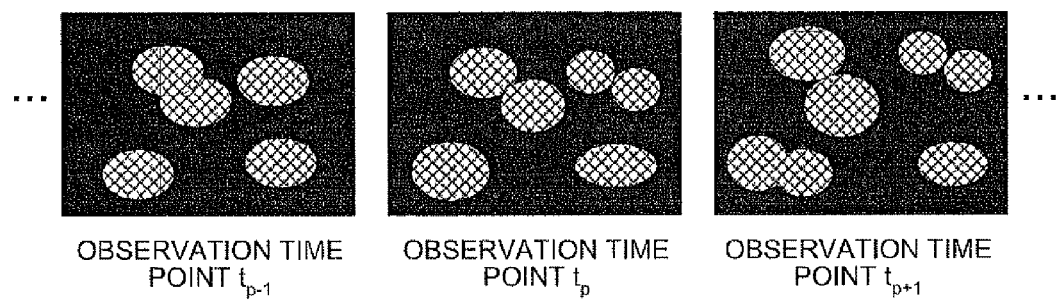
FIG. 2 is a diagram of an example of observation images input to the image processing apparatus.

The image processing unit 2 includes a pre-processing unit 2a, a recognition processing unit 2b, a characteristic amount measurement processing unit 2c, a tracking processing unit 2d, a division detection processing unit 2e, and a family tree generation processing unit 2f. The image processing unit 2 processes, as images input to the image processing apparatus 1, a series of observation images captured at a plurality of time points, in which a living cell is chronologically recorded. The series of observation images are, for example, fluorescence images of chronologically-recorded living cell to which fluorescence protein is introduced. As shown in FIG. 2, the living cells to be observed are shown with the dark background. The state of living cells shown in FIG. 2 is changed, i.e., the living cells move, expands, contract, modify, or divide during a period at observation time points $t_p$ to $t_{p+1}$ (p is an integer). The image processing apparatus 2 can process, as the observation images, phase contrast images obtained by observing the living cells based on the phase contrast.

The pre-processing unit 2a performs, as pre-processing, smoothing processing for removing noises while maintaining the edge, sharpening processing for highlighting the edge, etc. The recognition processing unit 2b performs cell recognition processing for recognizing, as a cell area, a cell image area corresponding to each living cell from the series of observation images on which the pre-processing unit 2a has performed the pre-processing. The recognition processing unit 2b adds, to each recognized cell area, a recognition label that is an identification index for individually identifying the cell area. The characteristic amount measurement processing unit 2c performs characteristic amount measurement processing for measuring cell characteristic amounts representing the characteristics of each cell area recognized by the recognition processing unit 2b.

The tracking processing unit 2d performs cell tracking processing for associating cell areas between the observation time points based on the cell characteristic amounts measured by the characteristic amount measurement processing unit 2c. Specifically, the tracking processing unit 2d determines whether a tracking target area that is a cell area whose image is captured at a target observation time point has an identity with a cell area whose image is captured at an observation time point earlier than the target observation time point based on the cell characteristic amounts. To the tracking target area having the identity, a tracking label serving as a tracking index indicating the identity is added. To the tracking target area not having the identity, a new tracking label serving as a new tracking index indicating that the cell area of the tracking target area is newly expressed. Because the tracking processing unit 2d sequentially performs the identity determination processing on an observation time point basis, the tracking label can be added to every cell area.

The division detection processing unit 2e performs cell division detection processing for detecting, from the cell areas recognized by the recognition processing unit 2b, a cell area on which it is determined that cell division has occurred in the living cell represented by the cell area. Specifically, the division detection processing unit 2e regards the cell area to which the tracking label is added as a target sell area to be processed, and measures relative position information indicating the relative position between the target cell area and a peripheral cell area around the target cell area. At least based on the relative position information, the division detection processing unit 2e determines whether cell division has occurred in the living cell represented by the target cell area, and detects the target cell area on which it is determined that cell division has occurred. The division detection processing unit 2e performs the processing on every cell area to which a tracking label is added.

The division detection processing unit 2e can determine whether cell division has occurred based on, in addition to the relative position information, the cell characteristic amounts of the target cell area and the cell characteristic amounts of an identical cell area to which the tracking label indicting the identity with the target cell area is added. The division detection processing unit 2e can determine whether cell division has occurred based on a tendency in variations in the cell characteristic amounts of the identical cell area whose image is captured at a time point earlier than that at which the image of the target cell area is captured.

The division detection processing unit 2e determines whether cell division has occurred based on a series of determination conditions based on the cell characteristic amounts and the relative position information. When the target cell area satisfies predetermined levels of the determination conditions among the determination conditions, the division detection processing unit 2e determines that cell division has occurred. The division detection processing unit 2e determines the levels of the determination conditions satisfied by the target cells area among the determination conditions. Depending on the determined levels, the division detection processing unit 2e adds, to the target cell area, a division label that is an index indicating the degree of possibility that cell division has occurred. Therefore, the cell areas to which the tracking labels are added can be classified to division levels corresponding to the division labels, i.e., to a plurality of levels corresponding to the degree of possibility that cell division have occurred.

Based on the relative position information, the cell characteristic amounts of the target cell area, and the cell characteristic amounts of the identical cell area, the division detection processing unit 2e detects a daughter cell area representing a daughter cell forming a pair with the living cell represented by the target cell area on which it is determined that cell division has occurred. The living cell represented by the target cell area on which it is determined that cell division has occurred is one of daughter cells expressed by the cell division. The daughter cell corresponding to the living cell, which is represented by the target cell area on which it is determined that cell division has occurred, is the other daughter cell generated by the cell division. The division detection processing unit 2e adds, to each of the cell areas representing the respective daughter cells, a parent-child label as an index indicating the relationship between the cell areas representing the daughter cells and the cell area indicating the parent cell, i.e, the parent-child relationship.

Based on the result of detection by the division detection processing unit 2e, the family tree generation processing unit 2f performs family tree generation processing for generating a family tree of the living cell indicated by the cell area on which it is determined that cell division has occurred. The family tree represents parent-child relationships between cells over at least two generations in the generation order. Information indicating the parent-child relationship over two generations is the minimum family tree. The family tree generation processing unit 2f adds, to the cell area indicating the parent cell, family tree information containing the family tree label indicating the observation time at which cell division has occurred and the daughter cell labels indicating the tracking labels of the respective daughter cells.

The display unit 3 includes, for example, a CRT, a liquid crystal display, or a projector, and it displays various types of information including the observation images, the processed images that are observation images having been processed by the image processing unit 2, various types of labels including the tracking labels, the parent-child labels, and the division labels, the cell characteristic amounts, the division levels, and the family trees. The processed images includes, for example, a cell image representing a cell area recognized by the recognition processing unit 2b, to which a tracking label is added by the tracking processing unit 2d. The display unit 3 includes a printer or the like, and it can print and display the various type of information.

The input unit 4 includes a USB, a communication interface based on, for example, the IEEE 1394, various types of switches, an input key, a mouse, and a touch panel, and it inputs various types of information. Specifically, the input unit 4 includes an observation image input unit 4a and a display item selecting unit 4b. The observation image input unit 4a inputs the series of observation images from an external device via, for example, the communication interface. The display item selecting unit 4b inputs display item selection information for selecting information displayed on the display unit 3 selected from the observation images, the processed images, the various types of labels the cell characteristic amounts, the division levels, and the family tree. By entering the display item selection information via the display item selecting unit 4b, an observer can arbitrarily select information to be displayed on the display unit 3.

The observation image input unit 4a includes an interface compatible with a storage medium such as a flash memory, a CD, a DVD, or a hard disk, and it can be configured to input an observation image stored in the storage medium. The observation image input unit 4a includes an imaging device including an imaging unit such as a CCD, and it can obtain a series of observation images by capturing observation images of a living cell observed via a microscope or the like.

The storage unit includes a ROM that previously stores therein various types of processing programs; and a RAM that stores therein processing parameters and processing data of each processing. Specifically, the storage unit 5 stores the series of observation images, the processed images, various types of information associated with each cell area and various types of processing programs executed by the control unit 6. The storage unit 5 can includes a storage medium such as a flash memory, a CD, a DVD, or a hard disk as a removable storage medium.

The control unit includes, for example, a CPU that executes the various types of programs stored in the storage unit 5, and it controls processing and operations of each constituent electrically connected in the image processing apparatus 1. Specifically, the control unit 6 includes an image processing control unit 6a and an image display control unit 6b, and it executes an image processing program stored in the storage unit 5. Specifically, the image processing control unit 6a controls the image processing performed by the image processing unit 2 and controls processing for inputting various types of information to the image processing unit 2 or outputting various types of information from the image processing unit 2. The image display control unit 6b causes the display unit 3 to display at least one of the observation images, the processed images, the various types of labels, the cell characteristic amounts, the division levels, and the family trees.

Figure 3:
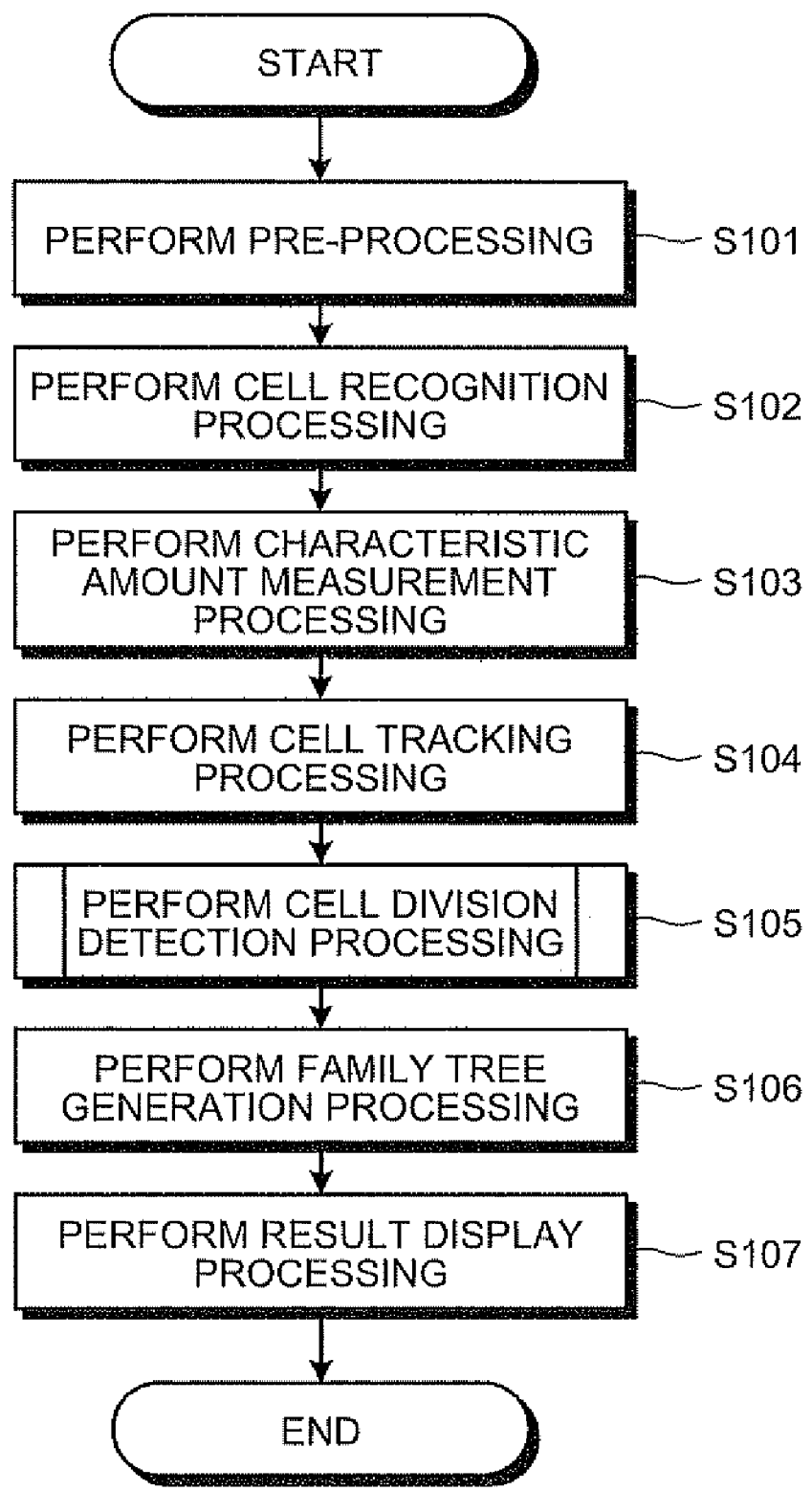
FIG. 3 is a flowchart of a process procedure performed by the image processing apparatus.

The process procedure performed by the image processing apparatus 1 is explained below. FIG. 3 is a flowchart of the process procedure for processing a series of observation images performed by the image processing apparatus 1 in response to execution of the image processing program by the control unit 6. First, the outline of the process procedure is explained with reference to FIG. 3.

The pre-processing unit 2a performs the pre-processing on the series of observation images read from the storage unit 5 by the image processing control unit 6a (step S101). The recognition processing unit 2b performs the cell recognition processing for recognizing individual cell areas from the series of observation images on which the pre-processing has been performed and for adding recognition labels to the individual cell areas (step S102). Subsequently, the characteristic amount measurement processing unit 2c performs the characteristic amount measurement processing for measuring cell characteristic amounts of each cell area (step S103). The tracking processing unit 2d performs the cell tracking processing for determining an identity of a cell area between observation time points and adding tracking labels to the cell areas (step S104).

Subsequently, the division detection processing unit 2e performs the cell division detection processing for determining whether cell division has occurred in a living cell represented by a cell area, detecting the cell area on which it is determined that cell division has occurred as a cell area representing one of daughter cells, and adding a division label to the detected cell area (step S105). At step S105, the division detection processing unit 2e further detects the other daughter cell and adds parent-child labels respectively to the cell areas representing the daughter cells.

Thereafter, the family tree generation processing unit 2f adds family tree information to the living cell that is the parent cell in which cell division has occurred, and performs the family tree generation processing for generating a family tree of the living cell (step S106). Based on display item selection information, the image display control unit 6b performs result display processing for displaying various types of information including the observation images, the processed images, the various types of labels, the cell characteristic amounts, the division levels, and the family tree (step S107), and the series of processes are completed. The image display control unit 6b can repeat step S107 depending on the display item selection information, which is sequentially updated, until, for example, predetermined instruction information for completing the processing is input.

The processing contents of steps S101 to S107 shown in FIG. 3 are more specifically explained below. First, at step S101, the pre-processing unit 2a performs the smoothing processing as the pre-processing on the series of observation images. In the smoothing processing, as shown in FIGS. 4-1 to 4-9, the pre-processing unit 2a refers a 5×5 pixel pattern PA including a target pixel OP to be processed in an observation image as a center and pixels near the target pixel OP. The pre-processing unit 2a sets a smoothing pixel value of the target pixel OP based on pixel value variances and averages calculated respectively for predetermined 3×3 pixel patterns in the 5×5 pixel pattern PA.

Specifically, the pre-processing unit 2a divides the 5×5 pixel pattern PA into nine types of 3×3 pixel patterns PA1 to PA9, and calculates a variance and an average of a plurality of hatched selected pixels of each of the 3×3 pixel patterns PA1 to PA9. The pre-processing unit 2a extracts a 3×3 pixel pattern showing the smallest variance, calculates an average value of pixel values of selected pixels of the extracted 3×3 pixel pattern, and sets the calculated average value as the smoothing pixel value of the target pixel OP. By performing the processing for setting a smoothing pixel value on each of the pixels of the observation image, the pre-processing unit 2a smoothes the observation image.

The number of pixels of a pixel pattern to be referred with respect to the target pixel OP is not limited to 5×5 pixels, and it can be reduced or increased.

The smoothing processing performed by the pre-processing unit 2a is not limited to the method described above. For example, pixel values of pixels near a target pixel in a predetermined area is referred, an average pixel value of pixels including a weighted center pixel is calculated, and the average pixel value is set s a smoothing pixel value of the target pixel. Alternatively, a smoothing pixel value can be set using the k most close averaging method. Alternatively, a smoothing pixel value can be set using a selection averaging method or smoothing can be performed using a known filter such as the median filter or the bilateral filter.

Furthermore, at step S101, the pre-processing unit 2a performs the sharpening processing for edge enhancement on the observation image on which the smoothing processing has been performed. In the sharpening processing, the pre-processing unit 2a weights a target pixel and pixels near the target pixel with, for example, a sharpening filter shown in FIG. 5 and obtains a total value of pixel values of weighted pixels. By sequentially performing the above operation processing on each pixel of the observation image, the pre-processing unit 2a sharpens the observation image. The series of processed images that are the observation images having been smoothed and sharpened by the pre-processing unit 2a are output by the image processing control unit 6a to the recognition processing unit 2b and recorded in the storage unit 5.

The cell recognition processing at step S102 is explained below. At step S102, the recognition processing unit 2b performs area division processing for dividing the pre-processed image, which is the processed image on which the pre-processing has been performed, into individual cell areas using, for example, the watershed method (see, for example, Non-Patent Document 1). According to Non-patent document 1, the watershed method is used to divide an image into areas in each of which low-luminance pixels are concentrated. However, because a cell is usually shown as a group of high-luminance pixels, the watershed method is adopted to divide an image into areas in each of which high-luminance pixels are concentrated, in which the luminance is inverted.

Because each of the areas divided by the watershed method is a cell area candidate, the recognition processing unit 2b verifies validity of the result of the division using luminance information. Specifically, the recognition processing unit 2b obtains a pixel having the highest luminance in each candidate area that is a divided cell area candidate. When the highest luminance is lower than a predetermined threshold $V_{tmin}$, the recognition processing unit 2b does not regard the candidate area as a cell area, and excludes the candidate area including other pixels belonging to the candidate area from targets of subsequent processing.

Furthermore, the recognition processing unit 2b compares the luminance of each pixel of the remaining candidate areas with a predetermined threshold $V_{pmin}$. Pixels smaller than the threshold are excluded from the candidate areas and not used for the subsequent processing. The recognition processing unit 2b regards each candidate area consisting of the pixels left as a result of the verification as a cell area, and adds a recognition label to each such cell area. In this manner, the recognition processing unit 2b recognizes cell areas from each of the pre-processed images, and adds the recognition label to each of the cell areas.

The series of cell images that are the processed images in which the cell areas have been recognized by the recognition processing unit 2b are output to the characteristic amount measurement processing unit 2c by the image processing control unit 6a and recorded in the storage unit 5.

The characteristic amount measurement processing at step S103 is explained below. At step S103, the characteristic amount measurement processing unit 2c measures, as the cell characteristic amounts of each cell area, the cell area's area, circularity, total luminance, average luminance, luminance standard deviation, area position, gravity center position, outline, etc. In addition, the circumference, fillet diameter, length, width, maximum luminance etc. can be measured. The cell characteristics measured by the characteristic amount measurement processing unit 2c are added to cell characteristic data on a cell area basis. The cell characteristic data updated by adding the cell characteristic amounts is recorded as update data in the storage unit 5 by the image processing control unit 6a. The updated cell characteristic data and the cell image are output to the tracking processing unit 2d.

The cell tracking processing at step S104 is explained below. At step S104, the tracking processing unit 2d calculates an evaluation value for evaluating relatedness between cell areas measured at different observation time points, and determines whether the cell areas have an identity with each other based on the evaluation value. First, the tracking processing unit 2d calculates an evaluation value J with the following Equation (1) using a distance $\delta_d$ between centers of gravity, an area difference $\delta_a$, a circularity difference $\delta_c$, and weighting coefficients $k_d$, $k_a$, and $k_c$ between cell areas $R_{t1,m}$ and $R_{t2,n}$ respectively at observation time points $t_1$ and $t_2$.

$$J = J(R_{t1,m}, R_{t2,n}) = k_d \cdot \delta_d + k_a \cdot \delta_a + k_c \cdot \delta_c \quad (1)$$

The variables m and n of Equation (1) are integers, and have relationships of $1 \leq m \leq M$ and $1 \leq n \leq N$ with numbers M and N of cell areas recognized in each of the cell images at the observation time points $t_1$ and $t_2$.

The smaller the evaluation value J is, the higher the relatedness between the cell areas $R_{t1,m}$ and $R_{t2,n}$ and the possibility that the cell areas $R_{t1,m}$ and $R_{t2,n}$ represent an identical cell are. Therefore, the tracking processing unit 2d calculates the evaluation value J on each possible combination of the variables m and n, and determines a cell area $R_{t1,m^\wedge}$ at the observation time point $t_1$ that leads a smallest evaluation value J with a cell area $R_{t2,n^\wedge}$ at the observation time point $t_2$.

$$R_{t1,m^\wedge}: \text{ where } J(R_{t1,m^\wedge}, R_{t2,n^\wedge}) = \min_{1 \leq m \leq M} J(R_{t1,m}, R_{t2,n^\wedge}) \quad (2)$$

When there are a plurality of variables m with which a smallest evaluation value J is obtained, the tracking processing unit 2d calculates a second evaluation value $J_2$ of the cell area $R_{t1,m}$ corresponding to the variables m, and obtains a combination of cell areas with which a smallest evaluation value $J_2$ is obtained as the cell areas $R_{t1,m^\wedge}$ and $R_{t2,n^\wedge}$. The tracking processing unit 2d calculates the evaluation value $J_2$ with the following Equation (3) using a total-luminance difference $\delta_s$, an average-luminance difference $\delta_m$, luminance-standard-deviation difference $\delta_v$, and predetermined weighting coefficients $k_s$, $k_m$, and $k_v$.

$$J_2 = J_2(R_{t1,m}, R_{t2,n}) = k_s \cdot \delta_s + k_m \cdot \delta_m + k_v \cdot \delta_v \quad (3)$$

When there are a plurality combinations of cell areas with which a smallest evaluation value $J_2$ is obtained, the image processing control unit 6a causes the display unit 3 to display the image data and the cell characteristic data corresponding to the combinations, and obtains, from the input unit 4, area combination information indicating a combination selected among the displayed combinations. The area combination information is, for example, entered by an operator of the image processing apparatus 1 via the input unit 4. The tracking processing unit 2d obtains the combination of the cell areas indicated by the area combination information as the cell areas $R_{t1,m^\wedge}$ and $R_{t2,n^\wedge}$.

Subsequently, the tracking processing unit 2d performs correction processing for minimizing errors in combinations of cell areas obtained as described above. Specifically, when the evaluation value J of the combination of the cell area $R_{t1,m^\wedge}$ at the observation time point $t_1$ and the cell area $R_{t2,n^\wedge}$ at the observation time point $t_2$ is larger than a predetermined threshold $V_{jmax}$, the tracking processing unit 2d regards the combination ineffective and determines that a cell area at the observation time point $t_1$ corresponding to the cell area $Rt_{2,n^\wedge}$ cannot be found. This occurs when, for example, the fluorescence protein introduced into the living cell to be observed firstly expresses at the observation time point $t_2$.

The tracking processing unit 2d determines that the cell area $R_{t1,m^\wedge}$ at the observation time point $t_1$ and the cell area $R_{t2,n^\wedge}$ at the observation time point $t_2$, which area obtained as described above, have an identity with each other, and adds, to the cell area $R_{t2,n^\wedge}$, an index indicating the identity with the cell area $R_{t1,m^\wedge}$, i.e., a tracking label $\Omega_i$ identical with that of the cell area $R_{t1,m^\wedge}$. If the identity determination processing is the firstly performed one in the cell tracking processing, because no tracking label has not been added to the cell area $R_{t1,m^\wedge}$, the tracking processing unit 2d adds the identical tracking labels $\Omega_i$ to both the cell area $R_{t1,m^\wedge}$ and the cell area $R_{t2,n^\wedge}$. The variable i of $\Omega_i$ is an integer, and has a relationship of $1 \leq i \leq R_{count}$ with a tracked cell total number $R_{count}$ that represents the total number of cell areas from the top observation time point $t_0$ the observation time point $t_2$ to each of which the tracking label is added.

The tracking processing unit 2d adds, to a cell area that newly expresses at a target observation time point in the identity determination processing, a new tracking label that has not been added to any cell area at any observation time point until just before the target observation time point. Therefore, the tracked cell total number $R_{count}$ is incremented as required. By performing the above an identity determination processing based on the series of observation time points, the tracking processing unit 2d can add the tracking label to every cell area.

The tracking label added by the tracking processing unit 2d is added to the cell characteristic data on a cell area basis. The cell characteristic data updated by adding the tracking label is recorded in the storage unit 5 as update data by the image processing control unit 6a. The updated cell characteristic data and the cell images are output to the division detection processing unit 2e.

The cell division detection processing at step S105 is explained below. At step S105, the division detection processing unit 2e classifies the individual cell areas to "division level $L_{num}$" using the total luminance, average luminance, area, circularity, a variation amount of the cell characteristic amounts, and the position characteristic amounts including the area position, gravity center position, and outline, and detects a cell area representing a cell area on which it is determined that cell division has occurred (hereinafter, "division cell area"). Explanation is provided with the premise that the level number "num" used as the subscript is an integer satisfying 1≦num≦4, and that the division detection processing unit 2e detects cell areas sorted into "division level L4" as division cell areas. Each division level serving as an index is added to a cell area representing a living cell corresponding to a daughter cell having expressed by cell division.

Figures 1, 4:
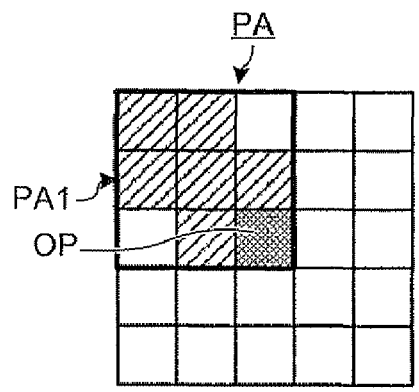
Figures 2, 4:
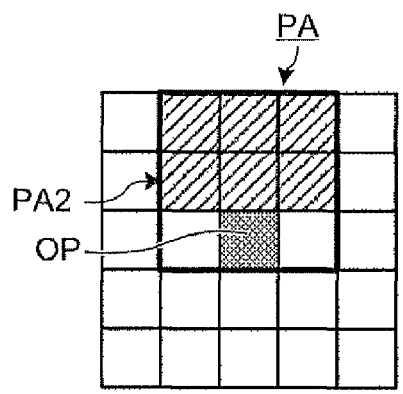
Figures 3, 4:
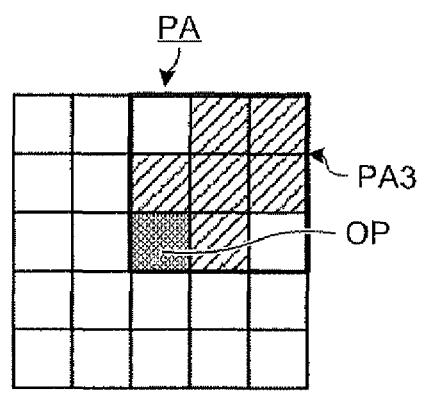
Figure 4:
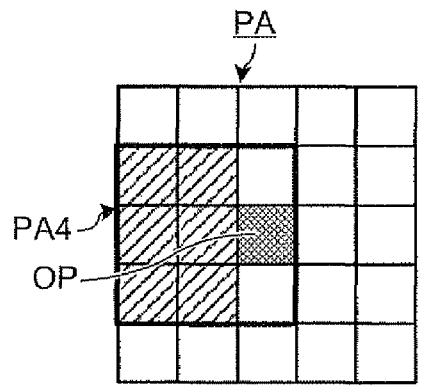
Figures 4, 5:
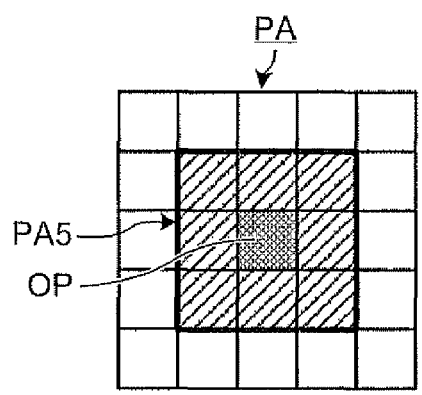
Figures 4, 5, 6:
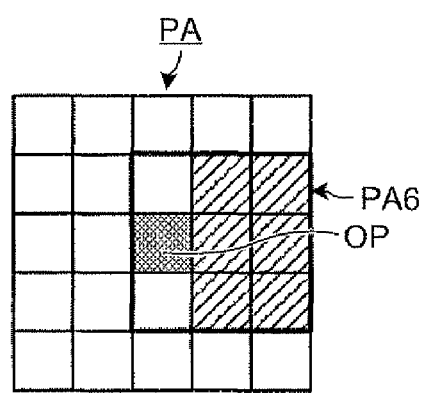

FIG. 6 is a flowchart of the process procedure of the cell division detection processing. As shown in FIG. 6, the cell division detection processing is performed using a series of seven determination conditions. The division detection processing unit 2e gradually narrows down the cell areas to cell areas highly likely to be division cell areas depending on whether each determination conditions is satisfied. The division detection processing unit 2e sorts the cell areas satisfying a total-luminance variation rate condition, an area position condition, and a circularity condition into "division level L1". Among the cell areas belonging to "division level L1", cell areas satisfying an average variation amount condition are sorted into "division level L2". Among the cell areas belonging to "division level L2", cell areas satisfying a new area expression condition and an area minimum distance condition are sorted into "division level L3". Finally, among the cell areas belonging to "division level L3", cell areas satisfying a similarity condition are sorted into "division level L4" and detected as division cell areas.

Details of each processing of the cell division detection processing are explained below with reference to FIG. 6. First, the division detection processing unit 2e selects cell areas high likely to be division cell areas based on the characteristic that the rate at which the total luminance of a cell area increases after cell division. Specifically, the division detection processing unit 2e obtains a total-luminance variation rate $VR_{tq},\Omega_i$ from the total luminance of each of the cell areas $R_{tp},\Omega_i$ and $R_{tq},\Omega_i$ having the tracking labels $\Omega_i$ at the observation time points $t_p$ and $t_q$. The variables p and q that are subscripts have a relationship of p<q. The total-luminance variation rate $VR_{tq},\Omega_i$ is calculated with the following Equation (4) using the total luminances $V_{tp},\Omega_i$ and $V_{tq},\Omega_i$ of the respective cell areas $R_{tp},\Omega_i$ and $R_{tq},\Omega_i$.

$$VR_{tq},\Omega_i = V_{tq},\Omega_i / V_{tp},\Omega_i \quad (4)$$

Figures 4, 5, 6, 7:
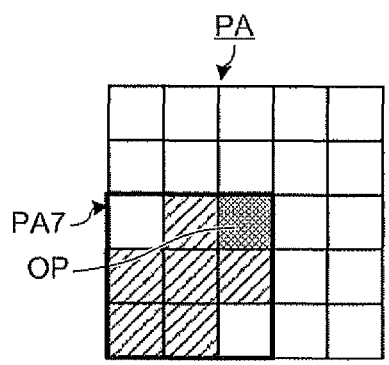
Figures 4, 5, 6, 7, 8:
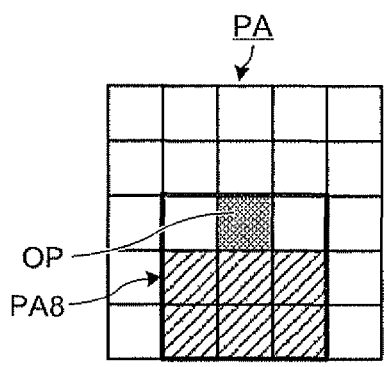
Figures 4, 5, 6, 7, 8, 9:
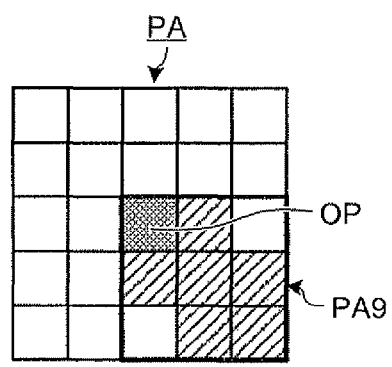
Figure 6:
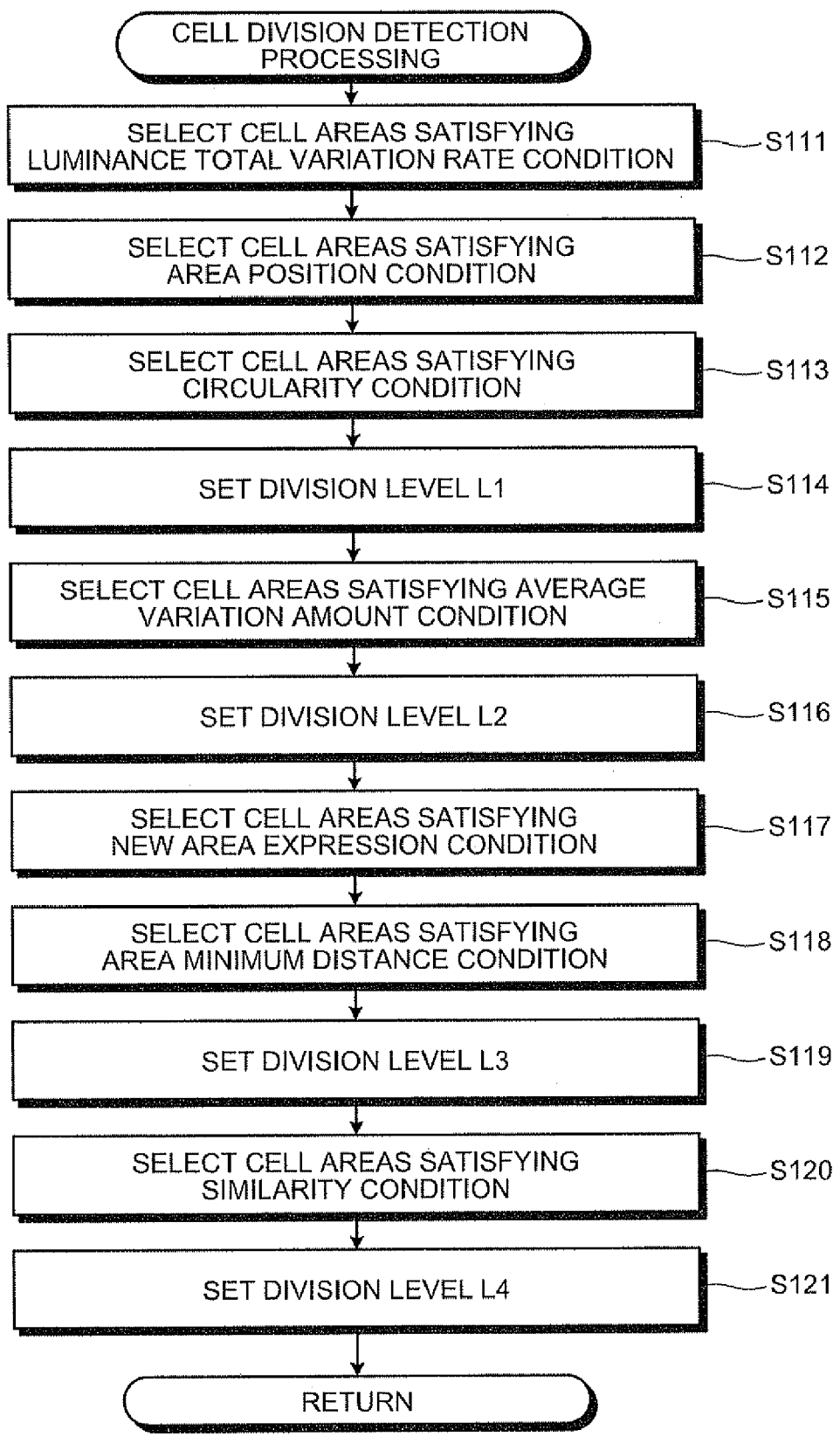
Figure 7:
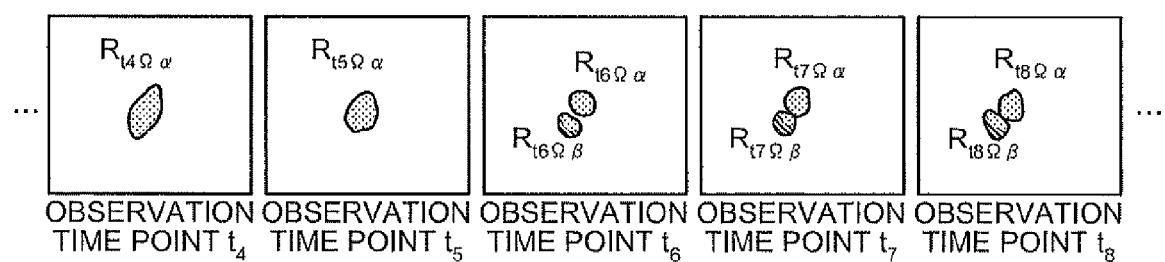
Figure 8:
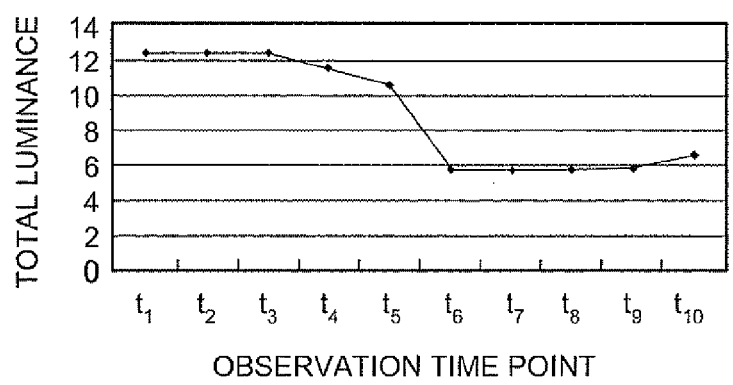
Figure 9:
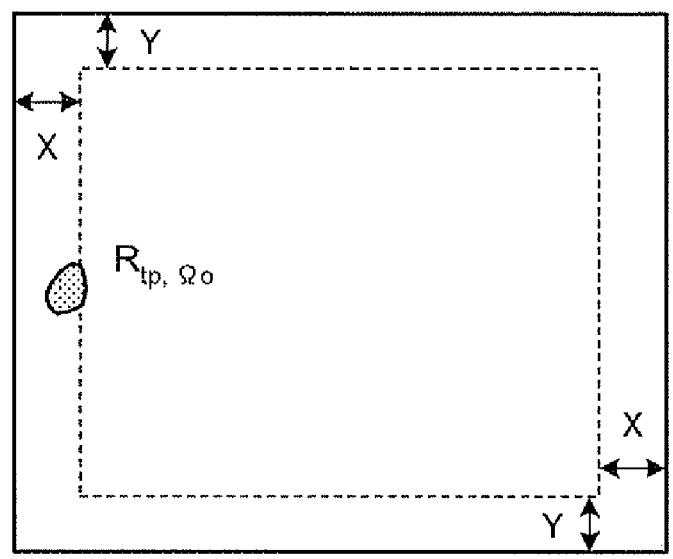

In cell division, protein formation starts at the last stage of division preparation, and the protein is equally allocated to two daughter cells at the division. For example, FIG. 7 shows cell images of cell areas $R_{tk},\Omega\alpha$ (4≦k≦8) having a tracking label $\Omega\alpha$ at observation time points $t_4$ to $t_8$. FIG. 8 is a graph of the total luminance of the cell area $R_{tk},\Omega\alpha$ (1≦k≦10) before and after cell division. From FIGS. 7 and 8, the cell area having the tracking label $\Omega\alpha$ divides into cell areas $R_{t6},\Omega\alpha$ and $R_{t6},\Omega\beta$ at the observation time point $t_6$, and it is confirmed that the total luminance significantly decreases. The variable k that is a subscript is an integer. In FIG. 7, the labels that identify respectively cell areas are added to the cell areas as character information.

The division detection processing unit 2e regards all cell areas to which the tracking label are added respectively as target cell areas to be processed at the series of observation time points, and sequentially calculates the total-luminance variation rates $VR_{tq},\Omega_i$ of the respective target cell areas to be processed. By determining whether each of the calculated total-luminance variation rates $VR_{tq},\Omega_i$ is within a predetermined total-luminance variation rate range VRange, the division detection processing unit 2e determines whether the total-luminance variation rate condition is satisfied.

In this manner, the division detection processing unit 2e selects cell areas that satisfy the total-luminance variation rate condition (step S111). The division detection processing unit 2e regards each cell area with the total-luminance variation rate $VR_{tq},\Omega_i$ within the total-luminance variation rate range VRange as a cell area satisfying the total-luminance variation rate condition, and leaves the cell area as a target cell area. On the other hand, the division detection processing unit 2e excludes a cell area on which it is determined that the total-luminance variation rate condition is not satisfied from the target cell areas. The total-luminance variation rate range VRange is set to one satisfying, for example, 0.4≦Vrange≦0.7 in consideration of the tendency that the total luminance of each cell area is easily influenced by capturing conditions and positional relationships with peripheral cells.

Subsequently, the division detection processing unit 2e further narrows down the cell areas satisfying the total-luminance variation rate condition to cell areas highly likely to be division cell areas based on the areas positions. Specifically, the division detection processing unit 2e determines whether each target cell area exists in a circumferential area of X pixels in the vertical direction and Y pixels in the horizontal direction from the vertical and horizontal ends on the cell image, and, based on the determination, determines whether the target cell area satisfies the area position condition. The numbers X and Y of pixels satisfy, for example, X=5 and Y=5.

In this manner, the division detection processing unit 2e selects cell areas satisfying the area position condition (step S112). The division detection processing unit 2e regards a cell area existing in the circumferential area as a cell area satisfying the area position condition, and leaves the cell area as a target cell area. On the other hand, the division detection processing unit 2e excludes a cell area not existing in the circumferential area, such as the cell area $R_{tq},\Omega_o$ shown in FIG. 9 as a cell area with possibility that the image of a part of the cell area is not captured. The division detection processing unit 2e adds, to the cell characteristic data about each excluded cell area, a cause label as an index indicating the cause. At step S112, the division detection processing unit 2e adds image end information $IME_{tq},\Omega_o$ as the cause label indicating that the area position condition is not satisfied.

Subsequently, the division detection processing unit 2e narrows down the cell areas satisfying the area position condition to cell areas highly likely to be division cell areas based on the circularity. Because the shape of a living cell becomes close to a sphere while contracting before cell division occurs, the circularity of the cell area representing the living cell becomes higher. Using the characteristics, the division detection processing unit 2e selects cell areas with high possibility that cell division has occurred.

Specifically, the division detection processing unit 2e detects a maximum circularity $MaxCir_{tq},\Omega_v$ of a cell area $R_{tq},\Omega_v$ having a tracking label $\Omega_v$ at the observation time point $t_q$, which is represented by the following Equation (5), based on each circularity $Cir_{t(q-j)},\Omega_v$ (j=1, 2, ..., cf) of the cell area $R_{tq},\Omega_v$ during a period from an observation time point $t_b$ earlier than the observation time point $t_q$ by a period corresponding to a predetermined number of frames to the observation time point $t_q$.

$$MaxCir_{tq},\Omega_v = \max(Cir_{t(q-j)},\Omega_v) \quad (5)$$

The division detection processing unit 2e determines whether the detected maximum circularity MaxCir$_{tq}$,Ω$_v$ is larger than a predetermined threshold CTh, and, based on the determination, determines whether the circularity condition is satisfied. The number cf of frames and the threshold CTh satisfy, for example, cf=5 and CTh=0.7.

In this manner, the division detection processing unit 2e selects cell areas satisfying the circularity condition (step S113). The division detection processing unit 2e regards each cell area with the maximum circularity MaxCir$_{tq}$,Ω$_v$ larger than the threshold CTh as a cell area satisfying the circularity condition, and leaves the cell area as a target cell area. On the other hand, the division detection processing unit 2e excludes a cell area on which it is determine that the circularity condition is not satisfied from the target cell areas. The division detection processing unit 2e adds, to the cell characteristic data about each excluded cell area, circularity insufficiency information CirError$_{tq}$,Ω$_v$ as a cause label indicating that the circularity condition is not satisfied.

It suffices that the observation time points $t_q$ and $t_b$ be observation time points at which cell areas having the identical label Ω$_v$ exist. In other words, the observation time points $t_q$ and $t_b$ are not necessarily successive depending on the capturing conditions and the positional relationship with other peripheral cell areas. In this case, the number cf of frames can be the counted number of frames in each of which a cell area having the tracking label Ω$_v$ exists.

As a result of steps S111 to S113, the division detection processing unit 2e sorts the target cell areas left as target cell areas into "division level L1", and adds, to the cell characteristic data of each of such cell areas, a division label $L_1$ as an index indicating that the cell area belongs to "division level L1" (step S114). In addition, the division detection processing unit 2e adds, to the characteristic data, a parent-child label GT$_{(tp,Ω_i),(tq,Ω_i)}$ that is an index indicating a relationship between the cell area R$_{tp}$,Ω$_i$ serving as the parent cell area representing the parent cell before cell division and the cell area R$_{tq}$,Ω$_i$ serving as the daughter cell area representing the daughter cell after cell division.

When a plurality of subscripts are added to each label, such as the recognition label, the tracking label, or the parent-child label, the left subscript is referred to as a first subscript and the second left subscript is referred to as the second subscript. A first subscript ($t_p$, Ω$_i$) of the parent-child label represents the observation time point $t_p$ at which the cell area is observed before cell division and the tracking label Ω$_i$ and a second subscript ($t_q$, Ω$_i$) represents the observation time point $t_q$ at which the cell area is observed after cell division and the tracking label Ω$_i$. This indicates that the tracking label same as that of the parent cell area is added to the daughter cell area. The characteristic data to which the division label, the parent-child label, the image end information, or the circularity insufficiency information by the tracking processing unit 2d is output by the image processing control unit 6a to the storage unit 5 and recorded therein as update data.

Subsequently, the division detection processing unit 2e narrows down the target cell areas sorted into "division level L1" to cell areas highly likely to be division cell areas based on an average variation amount of a predetermined cell characteristic amounts of the target cell area. A living cell shows a characteristic variation tendency in the average brightness, area, and circularity before cell division occurs. Specifically, variations in the average brightness tend to increase because of formation of fluorescence protein, variations in the area tend to increase because of the contraction, and variations in the circularity tend to increase because of modification to an approximate sphere. Using the characteristics, the division detection processing unit 2e selects cell areas highly likely to be division cell areas.

The division detection processing unit 2e obtains amounts of variations in an average luminance VA$_{t(q-j)}$,Ω$_i$, an area S$_{t(q-j)}$,Ω$_i$, and a circularity Cir$_{t(q-j)}$,Ω$_i$ of chronologically successive two frames of the cell area R$_{tq}$,Ω$_i$ having the tracking label Ω$_i$ at the observation time point $t_q$, in which the cell area exist, during a period from an observation time point $t_c$ earlier than the observation time point $t_q$ by a predetermined number d of frames to the observation time point $t_q$, and calculates averages of the amounts. The average luminance VA$_{t(q-j)}$,Ω$_i$, an average variation amount A_VA$_{tq}$,Ω$_i$ of average luminance, an average variation amount A_S$_{tq}$,Ω$_i$ of area, and an average variation amount A_Cir$_{tq}$,Ω$_i$ of circularity are calculated respectively using the following Equations (6) to (9), where a variable j is an integer satisfying j=1, 2, . . . , df.

$$VA_{t_{(q-j)},\Omega_i} = V_{t_{(q-j)},\Omega_i} / S_{t_{(q-j)},\Omega_i} \tag{6}$$

$$A\_VA_{t_{(q-j)},\Omega_i} = \sum_{s=t_c}^{s=t_{(q-1)}} \left(VA_{t_{(s+1)},\Omega_i} - VA_{t_s,\Omega_i}\right)/df \tag{7}$$

$$A\_S_{t_q,\Omega_i} = \sum_{s=t_c}^{s=t_{(q-1)}} \left(S_{t_{(s+1)},\Omega_i} - S_{t_s,\Omega_i}\right)/df \tag{8}$$

$$A\_Cir_{t_q,\Omega_i} = \sum_{s=1_c}^{s=t_{(q-1)}} \left(Cir_{t_{(s+1)},\Omega_i} - Cir_{t_s,\Omega_i}\right)/df \tag{9}$$

Subsequently, the division detection processing unit 2e determines whether each of the average variation amount A_VA$_{tq}$,Ω$_i$ of average luminance, the average variation amount A_S$_{tq}$,Ω$_i$ of area, and average variation amount A_Cir$_{tq}$,Ω$_i$ of circularity is a positive value or a negative value based on the following Inequalities (10) to (12), and, based on the determination, determines whether the average variation amount condition is satisfied.

$$A\_VA_{t_q,\Omega_i} \geq 0 \tag{10}$$

$$A\_S_{t_q,\Omega_i} \leq 0 \tag{11}$$

$$A\_Cir_{t_q,\Omega_i} \geq 0 \tag{12}$$

In this manner, the division detection processing unit 2e selects cell areas satisfying the average variation amount condition (step S115). The division detection processing unit 2e regards a cell area satisfying all Inequalities (10) to (12) as a cell area satisfying the average variation amount condition, and leaves the cell area as a target cell area. On the other hand, the division detection processing unit 2e excludes a cell area on which it is determined that the average variation amount condition is not satisfied from the target cell areas. While sorting the cell areas left as target cell area into "division level L2", the division detection processing unit 2e adds, to the cell characteristic data about each of the cell areas, a division label $L_2$ as an index indicating that the cell belongs to "division level L2" (step S116). The cell characteristic data to which the division label L2 is added is output by the image processing control unit 6a to the storage unit 5 and recorded therein as update data.

Depending on the capturing time point and the timing of cell division, significant variations in the cell characteristic amounts such as the total luminance, area, and circularity may be shown in observation images. In such a case, the variations in the total luminance, area, and circularity are small. For this reason, the division detection processing unit 2e sets an error range to values around "±0" of the respective average variation amounts represented by Equations (7) to (9). When the results of calculations with Equations (7) to (9) are within the error range, each average variation amount is set to "0".

The error range is determined based on a predetermined rate $E_{rate}$ with respect to an average of each cell characteristic amounts. An average $\Lambda\_VAve_s$ of average luminance, an average $\Lambda\_SAve_s$ of area, and an average of circularity $\Lambda\_CAve_s$ are calculated with the following Equations (13) to (15).

$$A\_VAve_s = \sum_{s=t_c}^{s=t_{(q-1)}} VA_{s,\Omega_i} / df \quad (13)$$

$$A\_SAve_s = \sum_{s=t_c}^{s=t_{(q-1)}} S_{s,\Omega_i} / df \quad (14)$$

$$A\_CAve_s = \sum_{s=t_c}^{s=t_{(q-1)}} Cir_{s,\Omega_i} / df \quad (15)$$

An error range $EV_{tq},\Omega_i$ with respect to the average of average luminance, an error range $ES_{tq},\Omega_i$ with respect to the average area, and an error range $EC_{tq},\Omega_i$ with respect to the average circularity are calculated using the following Equations (16) to (18) where a rate $E_{rate}$ satisfies, for example, $E_{rate}=0.005$ and the error range is set to 0.5% of the average of each cell characteristic amount.

$$EV_{tq},\Omega_i = (\Lambda\_VAve_s) \times E_{rate} \quad (16)$$

$$ES_{tq},\Omega_i = (\Lambda\_SAve_s) \times E_{rate} \quad (17)$$

$$EC_{tq},\Omega_i = (\Lambda\_CAve_s) \times E_{rate} \quad (18)$$

The division detection processing unit 2e performs error determination based on the following Equations (19) to (21) on the average variation amount $A\_VA_{tq},\Omega_i$ of average luminance, the average variation amount $A\_S_{tq},\Omega_i$ of area, and the average variation amount $A\_Cir_{tq},\Omega_i$ of circularity, which are respectively calculated using Equations (7) to (9), using Equations (13) to (15) and (16) to (18), and finally obtains each average variation amount at the observation time point $t_q$.

$$\text{if } |A\_VA_{tq},\Omega_i| < EV_{tq},\Omega_i \text{ then } A\_VA_{tq},\Omega_i = 0 \quad (19)$$

$$\text{if } |A\_S_{tq},\Omega_i| < ES_{tq},\Omega_i \text{ then } A\_S_{tq},\Omega_i = 0 \quad (20)$$

$$\text{if } |A\_Cir_{tq},\Omega_i| < EC_{tq},\Omega_i \text{ then } A\_Cir_{tq},\Omega_i = 0 \quad (21)$$

Subsequently, the division detection processing unit 2e narrows down the target cell areas sorted into "division level L2" to cell areas highly likely to be division cell areas based on whether there is a counterpart daughter cell area. The division detection processing unit 2e determines whether there is a counterpart daughter cell area based on whether there is a new cell area having newly expressed at the observation time point at which cell division is likely to occur, and selects cell areas highly likely to be division cell areas.

Specifically, using a total number $total_{r0,t(h-1)}$ of cells tracked from the tracking start observation time point $t_0$ an observation time point $t_{(h-1)}$ and a total number $total_{r0,th}$ of cells tracked from the observation time point to the observation time point $t_h$, the division detection processing unit 2e determines whether a new area number $NewR_{t(h-1),th}$ representing the number of new cell areas of a cell area $R_{th},\Omega\Phi$ sorted into "division level L2", which expresses at the observation time point $t_h$, satisfies the condition represented by the following Equation (22). Based on the determination, the division detection processing unit 2e determines whether the new area expression condition is satisfied. The subscript new of a new tracking label $\Omega_{new}$ added to a new cell area satisfies the following Inequality (23).

$$NewR_{t(h-1),th} = total_{r0,th} - total_{r0,t(h-1)} > 0 \quad (22)$$

$$(total_{r0,t(h-1)} + 1) \leq new \leq total_{r0,th} \quad (23)$$

In this manner, the division detection processing unit 2e selects cell areas satisfying the new area expression condition (step S117). The division detection processing unit 2e regards each cell area satisfying Equation (22) as a cell area satisfying the new area expression condition, and leaves the cell area as a target cell area. On the other hand, the division detection processing unit 2e excludes a cell area on which it is determined that the new area expression condition is not satisfied from the target cell areas. The division detection processing unit 2e adds, to the cell characteristic data about the excluded cell area, new area free information $NewError_{th},\Omega\Phi$ as a cause label indicating that the new area expression condition is not satisfied. The cell characteristic data to which the new area free information $NewError_{th},\Omega\Phi$ is added is output by the image processing control unit 6a to the storage unit 5 and recorded therein as update data.

The new area expression condition is a determination condition for detecting, without overdetection, a cell area on which it is likely that cell division has occurred. On the other hand, when the method is applied to the case where a new cell area is not recognized depending on the capturing conditions or the positional relationships with peripheral cells, the processing for selecting cell areas based on the new area expression condition can be omitted although it is highly likely that overdetection is caused.

Subsequently, the division detection processing unit 2e narrows down the target cell areas satisfying the new area expression condition to cell areas highly likely to be division cell areas based on the positional relationship between a cell area and a new cell area. The division detection processing unit 2e performs elliptic approximation on the cell area $R_{tq},\Omega_i$ that is the a target cell area at the observation time point $t_q$ and has the tracking label $\Omega_i$ to approximate the cell area $R_{tq},\Omega_i$ to the cell area $R_{tp},\Omega_i$ having the tracking label $\Omega_i$ at the observation time point $t_p$ just before cell division. Known methods can be used as an elliptic approximation method. In the embodiment, approximation method based on principal component analysis is used.

The covariance matrix $M_{tp},\Omega_i$ of the e11 area $R_{tp},\Omega_i$ is obtained with the following Equation (24) using a gravity center $g_{tp},\Omega_i$ and a pixel $p_{tp},\Omega_{i,k}$ (k=1, 2, ..., num) of the cell area $R_{tp},\Omega_i$. The gravity center $g_{tp},\Omega_i$ and the pixel $P_{tp},\Omega_{i,k}$ are represented respectively by Equations (25) and (26). The valuable num is an integer representing the number of pixels constituting the cell area $R_{tp},\Omega_i$. An upper subscript T of Equation (24) indicates that a matrix to which the subscript is added is converted to a transposed matrix.

$$M_{t_p,\Omega_i} = \frac{1}{num}\sum_{k=1}^{num}(p_{t_p,\Omega_i,k} - g_{t_p,\Omega_i})(p_{t_p,\Omega_i,k} - g_{t_p,\Omega_i})^T \quad (24)$$

$$= \frac{1}{num}\sum_{k=1}^{num}\begin{pmatrix} (x_k - g_x)(x_k - g_x) & (x_k - g_x)(y_k - g_y) \\ (y_k - g_y)(x_k - g_x) & (y_k - g_y)(y_k - g_y) \end{pmatrix}$$

$$= \begin{pmatrix} a_{11} & a_{12} \\ a_{21} & a_{22} \end{pmatrix}$$

$$p_{t_p,\Omega_i,k} = \begin{pmatrix} x_k \\ y_k \end{pmatrix} \quad (25)$$

$$g_{t_p,\Omega_i} = \begin{pmatrix} g_x \\ g_y \end{pmatrix} \quad (26)$$

The division detection processing unit 2e performs principal component analysis on the matrix $M_{t_p,\Omega_i}$, in which a principal component $e_{t_p,\Omega_i}$ is obtained with the following Equations (27) and (28) and the obtained principal component $e_{t_p,\Omega_i}$ is set as a long axis $La_{t_p,\Omega_i}$ of the cell area $R_{t_q,\Omega_i}$.

$$e_{t_p,\Omega_i} = a \cdot \cos^2\theta + 2\cos\theta \cdot \sin\theta + a_{22} \cdot \sin^2\theta \quad (27)$$

$$\theta = (1/2) \cdot \tan^{-1}(2a_{12}/(a_{11}-a_{22})) \quad (28)$$

Figure 10:
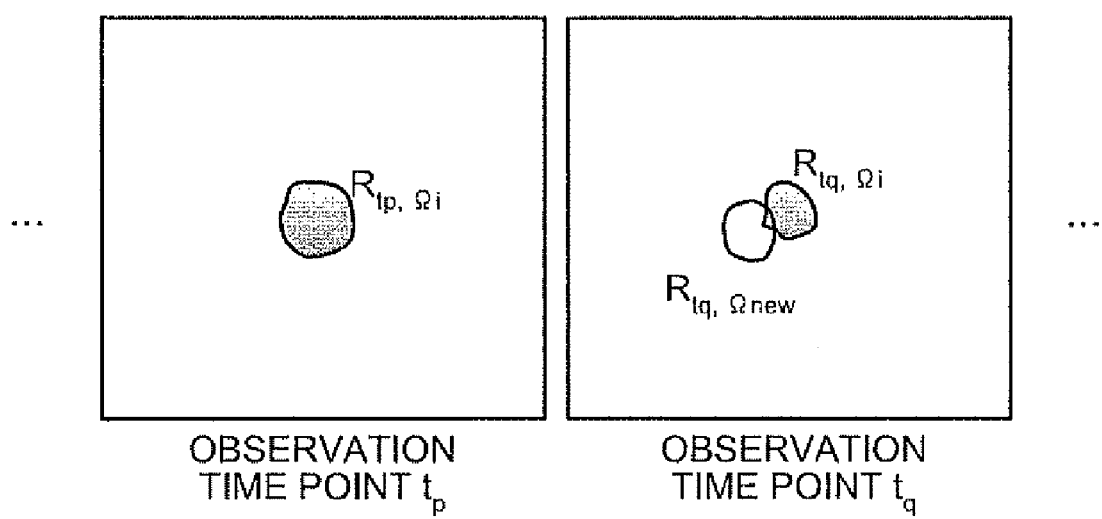
FIG. 10 is a diagram exemplarily showing cell images representing a cell area in which cell division has occurred.
Figures 1, 11:
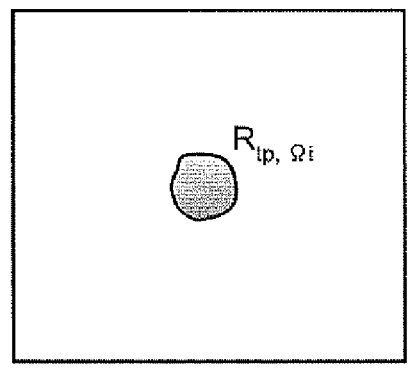
Figures 2, 11:
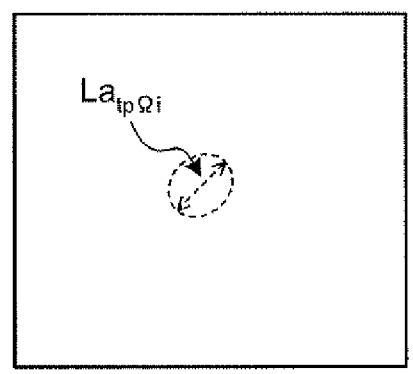
Figures 3, 11:
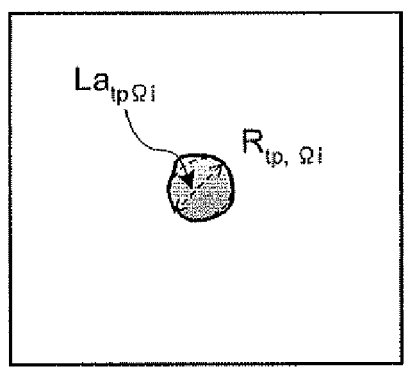

FIG. 10 is a diagram of cell images of the cell areas $R_{t_p,\Omega_i}$ and $R_{t_q,\Omega_i}$ at observation time points $t_p$ and $t_q$. FIGS. 11-1 to 11-3 are diagrams representing how elliptic approximation is performed. FIG. 11-1 shows a cell image, FIG. 11-2 shows the result of elliptic approximation on the cell area $R_{t_p,\Omega_i}$, and FIG. 11-3 shows the state where the cell image and the result of elliptic approximation are overlapped. In the images shown in FIGS. 10 and 11-1 to 11-3, the label for identifying the cell area and the label indicating the long axis of the approximated ellipse are added as character information.

The division detection processing unit 2e calculates a distance $\Delta_k$ between a center gravity $g_{t_q,\Omega_i}$ of the cell area $R_{t_q,\Omega_i}$ and each pixel $ContourP_{t_q,\Omega_{new},k}$ (k=1, 2, ..., τ) constituting the outline of a new cell area $R_{t_q,\Omega_{new}}$ having the new tracking label $\Omega_{new}$ having expressed at the observation time point $t_q$, and obtains a minimum distance $\delta_{t_q,\Omega_i,\Omega_{new}}$ representing the minimum value. The distance $\Delta_k$ is calculated with Equation (29) using the center gravity $g_{t_q,\Omega_i}$ and the pixel $ContourP_{t_q,\Omega_{new},k}$ respectively represented by Equations (30) and (31). In addition, the minimum distance $\delta_{t_q,\Omega_i,\Omega_{new}}$ is obtained based on Equation (32).

$$\Delta_k = \sqrt{(C_{kx} - g_x)^2 + (C_{ky} - g_y)^2} \quad (29)$$

$$g_{t_q,\Omega_i} = \begin{pmatrix} g_x \\ g_y \end{pmatrix} \quad (30)$$

$$ContourP_{t_q,\Omega_i,k} = \begin{pmatrix} C_{kx} \\ C_{ky} \end{pmatrix} \quad (31)$$

$$\delta_{t_q,\Omega_i,\Omega_{new}} = \min(\Delta_k) \quad (32)$$

Figure 12:
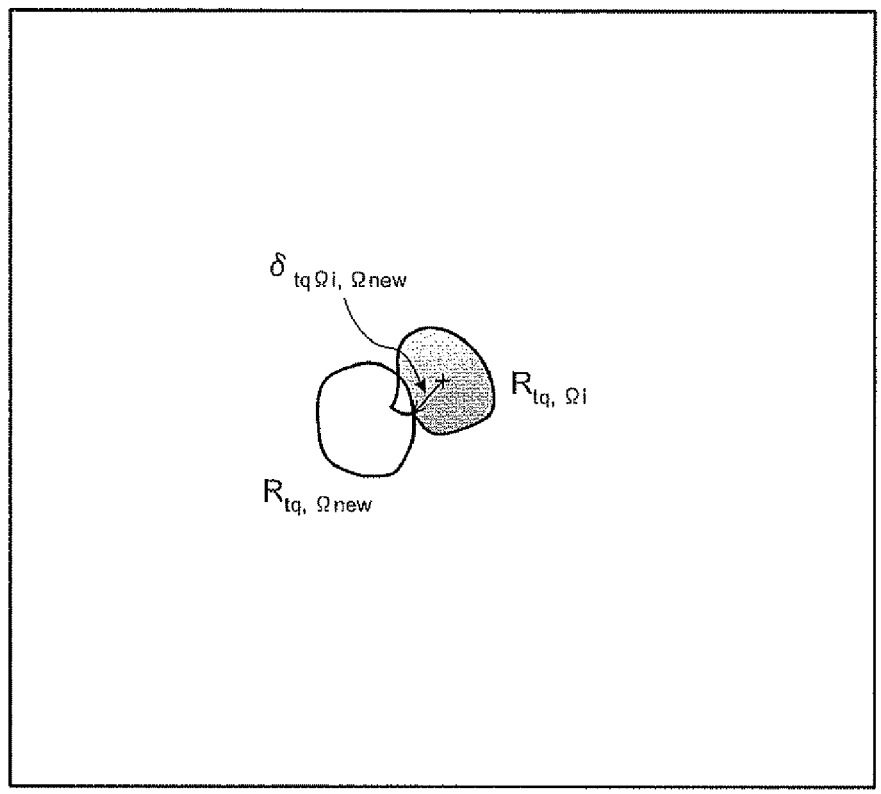
FIG. 12 is a diagram for explaining determination processing based on a new area expression condition.

FIG. 12 shows the minimum distance $\delta_{t_q,\Omega_i,\Omega_{new}}$ obtained by performing elliptic approximation as described above.

Based on the result of the above operation, the division detection processing unit 2e determines whether the minimum distance $\delta_{t_q,\Omega_i,\Omega_{new}}$ is not larger than the long axis $La_{t_p,\Omega_i}$ of the cell area $R_{t_p,\Omega_i}$, and, based on the determination, determines whether the area minimum distance condition is satisfied. In this manner, the division detection processing unit 2e selects cell areas satisfying the area minimum distance condition (step S118). The division detection processing unit 2e regards the cell area $R_{t_q,\Omega_i}$ with the minimum distance $\delta_{t_q,\Omega_i,\Omega_{new}}$ not larger than the long axis $La_{t_p,\Omega_i}$ as a cell area satisfying the area minimum distance condition, and leaves the cell area $R_{t_q,\Omega_i}$ as a target cell area. On the other hand, the division detection processing unit 2e excludes the cell area not satisfying the area minimum distance condition from the target cell areas.

The division detection processing unit 2e sorts the cell area $R_{t_q,\Omega_i}$ left as a target cell area into "division level L3", and adds, to the cell characteristic data of each of such cell areas, a division label $L_3$ as an index indicating that the cell area belongs to "division level L3" (step S119). In addition, the division detection processing unit 2e adds, to the characteristic data of the new cell area $R_{t_q,\Omega_{new}}$, a parent-child label $GT_{(t_p,\Omega_i),(t_q,\Omega_{new})}$ that is an index indicating that the new cell area $R_{t_q,\Omega_{new}}$ is a daughter cell area representing another daughter cell having expressed from the parent cell that is the living cell represented by the cell area $R_{t_q,\Omega_i}$. The cell characteristic data to which the division label $L_3$ or the parent-child label $GT_{(t_p,\Omega_i),(t_q,\Omega_{new})}$ is added is output by the image processing control unit 6a by to the storage unit 5 and recorded therein as update data.

The positional relationship between the target cell area and the new cell area can be determined based on the long axis direction of the target cell area in addition to the minimum distance. From the new cell areas having newly expressed in the long axis direction of a cell area $R_{t_p,\Omega_{i'}}$ at the observation time point $t_p$ just before cell division, a cell area $R_{t_q,\Omega_{i'}}$ with the minimum distance from the cell area $R_{t_p,\Omega_{i'}}$ can be detected. When the minimum distance $\delta_{t_q,\Omega_{i'},\Omega''}$ is not larger than a predetermined threshold, the cell area $R_{t_q,\Omega_{i''}}$ is sorted into "division level L3". In addition, the cell area $R_{t_q,\Omega_{i''}}$ is regarded as a daughter cell area representing the other daughter cell expressing from the living cell represented by the cell area $R_{t_p,\Omega_{i''}}$. Alternatively, determination can be made based on the direction in which two mitotic spindles formed of microtubules connect to each other just before cell division. In this case, it is recommended that the living cell to be observed is labeled such that the microtubules can be identified.

Subsequently, the division detection processing unit 2e narrows down the target cell areas sorted into "division level L3" to cell areas highly likely to be division cell areas based on similarity to the new cell area that is a daughter cell area representing a counterpart daughter cell area. Specifically, using an average luminance $VA_{t_q,\Omega_i}$, an area $S_{t_q,\Omega_i}$, and a circularity $Cir_{t_q,\Omega_i}$ of the cell area $R_{t_q,\Omega_i}$ and an average luminance $VA_{t_q,\Omega_{new}}$, an area $S_{t_g,\Omega_{new}}$, and a circularity $Cir_{t_q,\Omega_{inew}}$ of the new cell area $R_{t_q,\Omega_{new}}$ at the observation time point $t_q$, the division detection processing unit 2e calculates the rates of the cell characteristic amounts between the cell areas with the following Equations (33) to (35).

$$\text{rate\_}VA_{t_q,\Omega_i,\Omega_{new}} = VA_{t_q,\Omega_{new}}/VA_{t_q,\Omega_i} \quad (33)$$

$$\text{rate\_}S_{t_q,\Omega_i,\Omega_{new}} = S_{t_q,\Omega_{new}}/S_{t_q,\Omega_i} \quad (34)$$

$$\text{rate\_Cir}_{t_q,\Omega_i,\Omega_{new}} = Cir_{t_q,\Omega_{new}}/Cir_{t_q,\Omega_i} \quad (35)$$

Based on the result of the operation, the division detection processing unit 2e calculates a similarity $Sim_{t_q,\Omega_i,\Omega_{new}}$ between the cell area $R_{t_q,\Omega_i}$ and the new cell area $R_{t_q,\Omega_{new}}$ as an average value of the ratios of the cell characteristic amounts with the following Equation (36).

$$Sim_{t_q,\Omega_i,\Omega_{new}} = (\text{rate\_}VA_{t_q,\Omega_i,\Omega_{new}} + \text{rate\_}S_{t_q,\Omega_i,\Omega_{new}} + \text{rate\_Cir}_{t_q,\Omega_i,\Omega_{new}})/3 \quad (36)$$

Thereafter, the division detection processing unit 2e determines whether the similarity $Sim_{tq,\Omega_i,\Omega_{new}}$ is within the range of a predetermined threshold Sim_Th, and, based on the determination, determines whether the similarity condition is satisfied. The predetermined threshold Sim_Th satisfies, for example, $0.7 \leq Sim\_Th \leq 1.3$.

In this manner, the division detection processing unit 2e selects cell areas satisfying the similarity condition (step S120). The division detection processing unit 2e regards the cell area $R_{tq},\Omega_i$ with the similarity $Sim_{tq,\Omega_i,\Omega_{new}}$ within the range of the predetermined threshold Sim_Th, and leaves the cell area $R_{tq},\Omega_i$ as a target cell area. On the other hand, the division detection processing unit 2e excludes a cell area on which it is determined that the similarity condition is not satisfied from the target cell areas. The division detection processing unit 2e sorts the cell area $R_{tq},\Omega_i$ left as a target cell area into "division level L4", and adds, to the cell characteristic data about each of such cell areas, a division label $L_4$ as an index indicating that the cell area belongs to "division level L4" (step S121). Finally, the division detection processing unit 2e detects each of the cell areas sorted into "division level L4" as a division cell area. The cell characteristic data to which the division label $L_4$ is added is output by the image processing control unit 6a to the storage unit 5 and recorded therein as update data.

By performing the cell division detection processing at step S105 as described above, in the image processing apparatus 1, division cell areas can be specified and detected and parent-child relationships between living cells recorded in observation images at different observation time points can be known from parent-child labels recorded in cell characteristic data.

In the process procedure of the cell division detection processing shown in FIG. 6, the division detection processing unit 2e can omit the processing corresponding to a part of determination conditions depending on, for example, the condition in which images of living cells represented by target cell areas are captured. For example, when the number of cells represented in an observation image is small and the shapes of living cells are clearly shown while the cells do not concentrate, the processing for selecting cell areas based on the average variation amount condition (step S115) can be omitted. This allows the division detection processing unit 2e to achieve high-speed cell division detection processing without lowering detection accuracy.

The division detection processing unit 2e can increase or decrease the number of division levels depending on the condition in which images of living cells represented by target cells are captured. For example, when living cells recorded in an observation image do not concentrate, the division detection processing unit 2e can set the level number num of "division level $L_{num}$" to one satisfying $1 \leq num \leq 3$, and detect cell areas sorted into "division level L3" as division cell areas. In other words, the cell division detection processing can be performed based on the area minimum distance condition as the last determination condition without selection cell areas based on the similarity condition for sorting cell areas into "division level L4".

The family tree generation processing at step S106 is explained below. At step S106, the family tree generation processing unit 2f generated a family tree of a living cell, referring to the parent-child label recorded in the cell characteristic data of each pixel area. When the cell area $R_{tq},\Omega_i$ at the observation time point $t_q$ sorted into "division level L4" has the parent-child label $GT_{(tp,\Omega_i),(tq,\Omega_i)}$, first, the family tree generation processing unit 2f retrieves the parent-child label with the first subscript $(t_q, \Omega_i)$ indicating information about the parent cell from the cell characteristic data belonging to the observation time point $t_p$.

If the parent-child label $GT_{(tp,\Omega_i),(tq,\Omega_{new})}$ is detected, the family tree generation processing unit 2f detects, based on the second subscript $(t_q, \Omega_{new})$ indicating the information about the daughter cell, the cell area $R_{tq},\Omega_{new}$ as the other daughter cell area representing the daughter cell. Thereafter, the family tree generation processing unit 2f adds, to the cell characteristic data about the parent cell area $R_{tp},\Omega_i$, family tree information indicating the parent-child relationship between the parent cell area $R_{tp},\Omega_i$ and the daughter cell areas $R_{tq},\Omega_i$ and $R_{tq},\Omega_{new}$. The cell characteristic data to which the family tree information is added is output by the image processing control unit 6a to the storage unit 5 and recorded therein as update data.

The family tree information consists of three labels: a family tree label Tree, a first daughter cell label daughter_1, and a second daughter cell label daughter_2. When daughter cell areas belonging to "division level L4" are associated with a parent cell area, the family tree label Tree has a value of the observation time point $t_q$ at which it is likely that cell division occurred (Tree=$t_q$), and has "0" as a value (Tree=0) in other cases.

When the family tree label Tree is not "0", the first daughter cell label daughter_1 and the second daughter cell label daughter_2 respectively have values of recognition labels $R_{tq},\Omega_i$ and $R_{tq},\Omega_{new}$ of the cell areas (daughter_1=$R_{tq},\Omega_i$, daughter_2=$R_{tq},\Omega_{new}$). In other words, the first daughter cell label daughter_1 has the recognition label of the daughter cell area succeeding the tracking label of the parent cell area, and the second daughter cell label daughter_2 has the recognition label of the daughter cell area newly having expressed. On the other hand, when the tree label Tree is "0", both the first daughter cell label daughter_1 and the second daughter cell label daughter_2 are "0".

The result display processing at step S107 is explained below. At step S107, the image display control unit 6b generates display data from the observation images at the series of observation time points, the processed images, the cell characteristic data stored in the storage unit 5, etc. The display data consists of the display images, family tree information, and cell characteristic data etc. necessary for confirming the cell areas and the result of tracking. The image display control unit 6b outputs the generated display data to the display unit 3 and causes the display unit 3 to display the display data.

Figure 13:
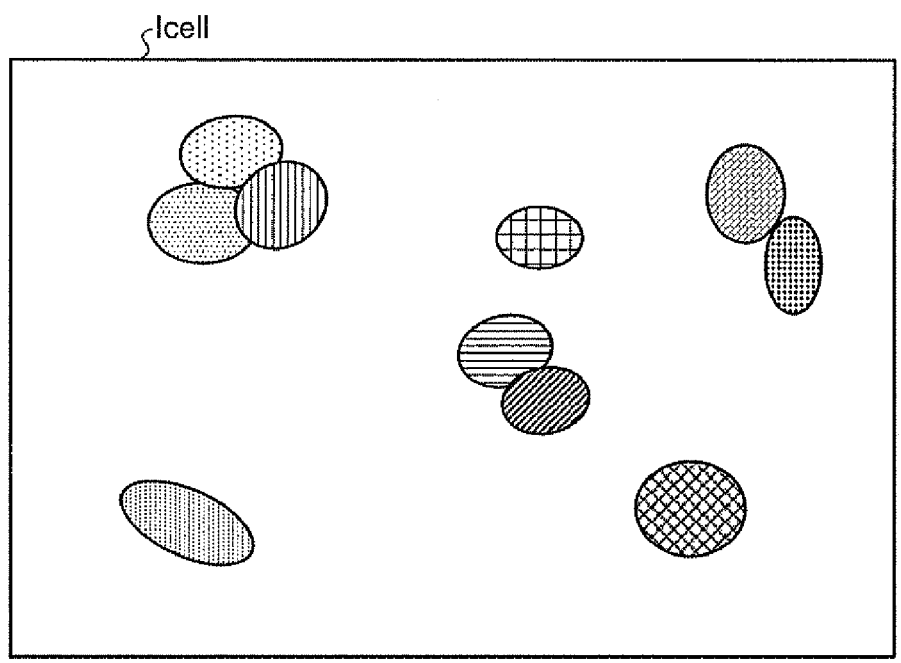
FIG. 13 is a diagram of an example of a cell display image.
Figure 14:
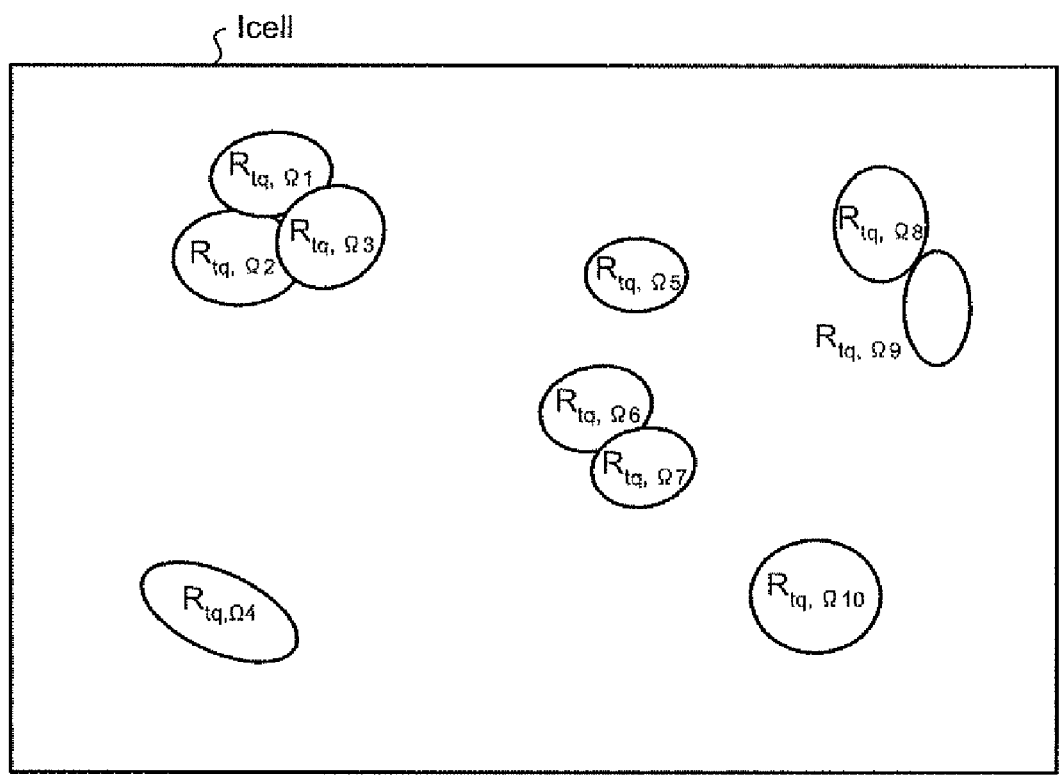
FIG. 14 is a diagram of an example of a cell display image.

FIG. 13 is a diagram of an example of a cell display image Icell as a display image in which cell areas are displayed. As shown in FIG. 13, the image display control unit 6b displays the cell areas respectively, for example, in different display patterns in the cell display image Icell. Alternatively, the cell areas can be displayed respectively with different display luminance, different types of outlines, or the like. FIG. 14 is another example of the cell display image Icell. As shown in FIG. 14, the image display control unit 6b can add the recognition labels as character information in association with cell areas, respectively.

Alternatively, the image display control unit 6b can display, for example, a superposed image obtained by superposing an observation image and a processed image, a superposed cell image obtained by chronologically superposing cell images at a plurality of observation time points. In an observation image that is a superposed image, a cell area that is not recognizable to human eyes can be made visible by adjusting the brightness of the cell area. By use of different display methods on an observation time point basis, a superposed cell image can be displayed such that chronological changes are visually distinguishable.

Figure 15:
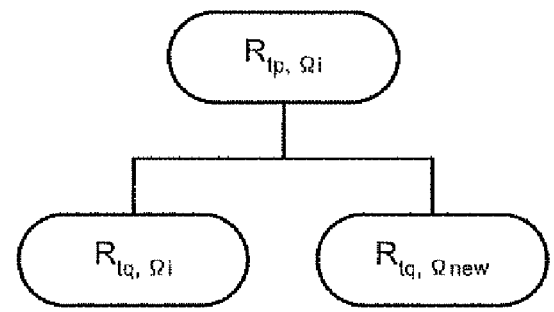
FIG. 15 is a diagram of an example of a family tree.

On the other hand, the image display control unit 6b displays a family tree of a living cell in which cell division has occurred in, for example, in a tree diagram as shown in FIG. 15. FIG. 15 shows the family tree of the cell area $R_{tp},\Omega_i$ with the family tree label satisfying Tree=$t_q$. As shown in FIG. 15, the image display control unit 6b represents the recognition label of the parent cell area $R_{tp},\Omega_i$ as the root of the family tree and the recognition labels of the daughter cell areas $R_{tq},\Omega_i$ and $R_{tq},\Omega_{new}$ at the end points of the family tree.

In addition to displaying cell characteristic data as a list, the image display control unit 6b can display the cell characteristic amounts including the total luminance and area that chronologically change as a chart in which the vertical axis represents time and the horizontal axis represents the characteristic amount.

The image display control unit 6b generates display data to be displayed by the display unit 3 based on the display item selection information. The display item selection information is updated every time when the display item selecting unit 4b inputs display item selection information, and the image display control unit 6b appropriately updates the display data based on the display item selection information.

The image display control unit 6b can display a desired cell area to be confirmed in a display image as a highlighted cell area based on selection information entered from an observer, for example, using a mouse via the input unit 4, and display arbitral display data from a table or a chart of the family tree information and the cell characteristic data corresponding to the highlighted cell area in synchronization with the cell area. In this case, when the observer selects, from the display image, the cell area of the display image or at least one of the end point and route of the family tree and the table and chart of the cell characteristic data, other corresponding display data can be displayed as highlighted data in addition to the selected one. The parent-child relationship can be easily understood by highlighting the parent, child, ancestors, and descendants of the family tree of the cell area corresponding to at least the selected display data.

As explained above, in the image processing apparatus 1 according to the first embodiment, cell areas representing individual living cells can be recognized from a series of observation images captured at a plurality of observation time points, in which a living cell is chronologically recorded, and cell areas representing an identical living cell can be tracked over the series of observation time points. In addition, division cell areas can be accurately specified and detected. Furthermore, various types of information about the observation images, processed images, cell characteristic data, and family tree of a cell area can be recognizably displayed based on an observation time point basis and a living cell basis.

Second Embodiment

A second embodiment of the present invention is explained below. In the second embodiment, after observation images are processed as in the case of the first embodiment described above, the result of classifying cell areas to a plurality of division levels can be modified based on determination by an observer.

Figure 16:
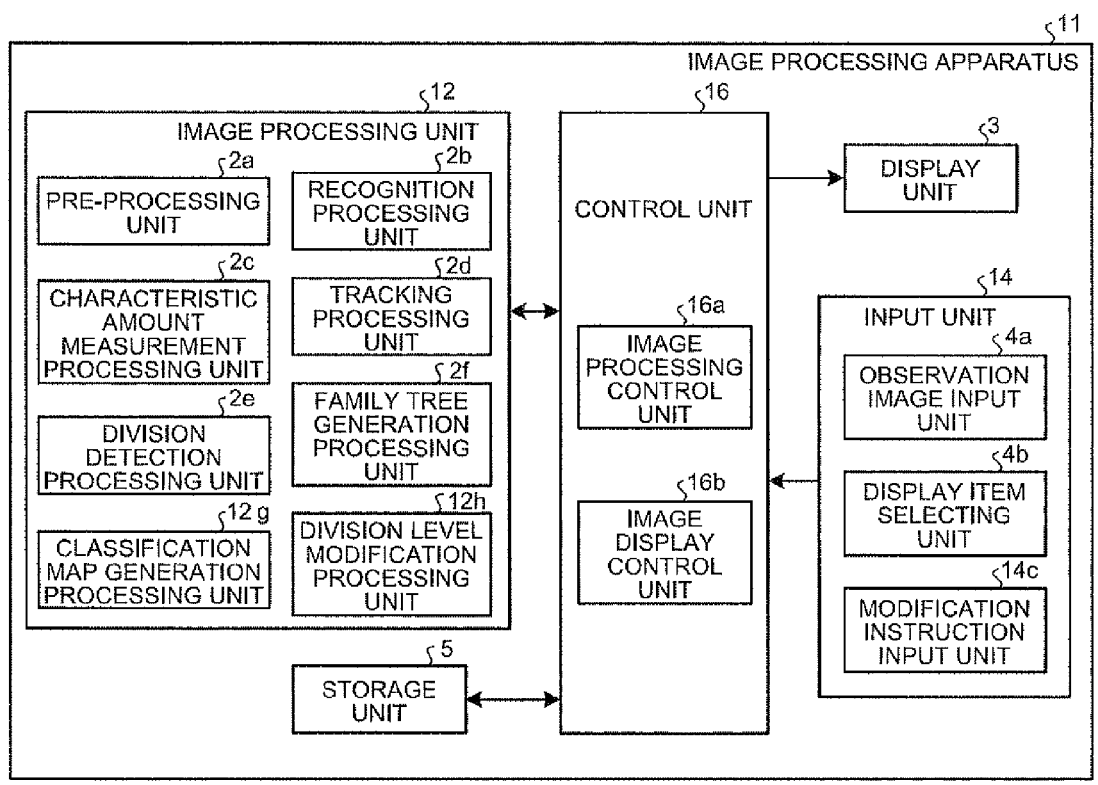
FIG. 16 is a block diagram of a configuration of an image processing apparatus according to a second embodiment of the present invention.

FIG. 16 is a block diagram of a configuration of an image processing apparatus 11 according to the second embodiment. As shown in FIG. 16, the image processing apparatus 11 basically has the same configuration as that of the image processing apparatus 1 and includes an image processing unit 12, an input unit 14, and a control unit 16 instead of the image processing unit 2, the input unit 4, and the control unit 6. The image processing unit 12 includes a classification map generation processing unit 12g and a division level modification processing unit 12h in addition to the constituents of the image processing unit 2. The input unit 14 includes a modification instruction input unit 14c in addition to the constituents of the input unit 4. Similar to the control unit 6, the control unit 16 includes an image processing control unit 16a and an image display control unit 16b. Other constituents are same as those of the first embodiment and the same constituents are denoted by the same reference numerals.

Based on the result of detection by the division detection processing unit 2e, the classification map generation processing unit 12g generates a division level classification map representing cell areas sorted into the levels from "division level L1" to "division level L4", in which the cell areas are classified on a division level basis. The division level classification map is output by the image display control unit 16b to the display unit 3 and displayed thereon.

The division level modification processing unit 12h modifies division labels $L_1$ to $L_4$ recorded in cell characteristic data about each cell area based on division level modification instruction information input from the modification instruction input unit 14c. The division level modification instruction information is, for example, entered by an observer who has referred to the division level classification map displayed on the display unit 3 via the modification instruction input unit 14c.

As the image processing control unit 6a does, the image processing control unit 16a controls image processing performed by the image processing unit 12 and processing for inputting various types of information to the image processing unit 12 or outputting various types of information from the image processing unit 12. As the image display control unit 6b does, the image display control unit 16b causes the display unit 3 to display various types of information processed by the image processing unit 12.

Figure 17:
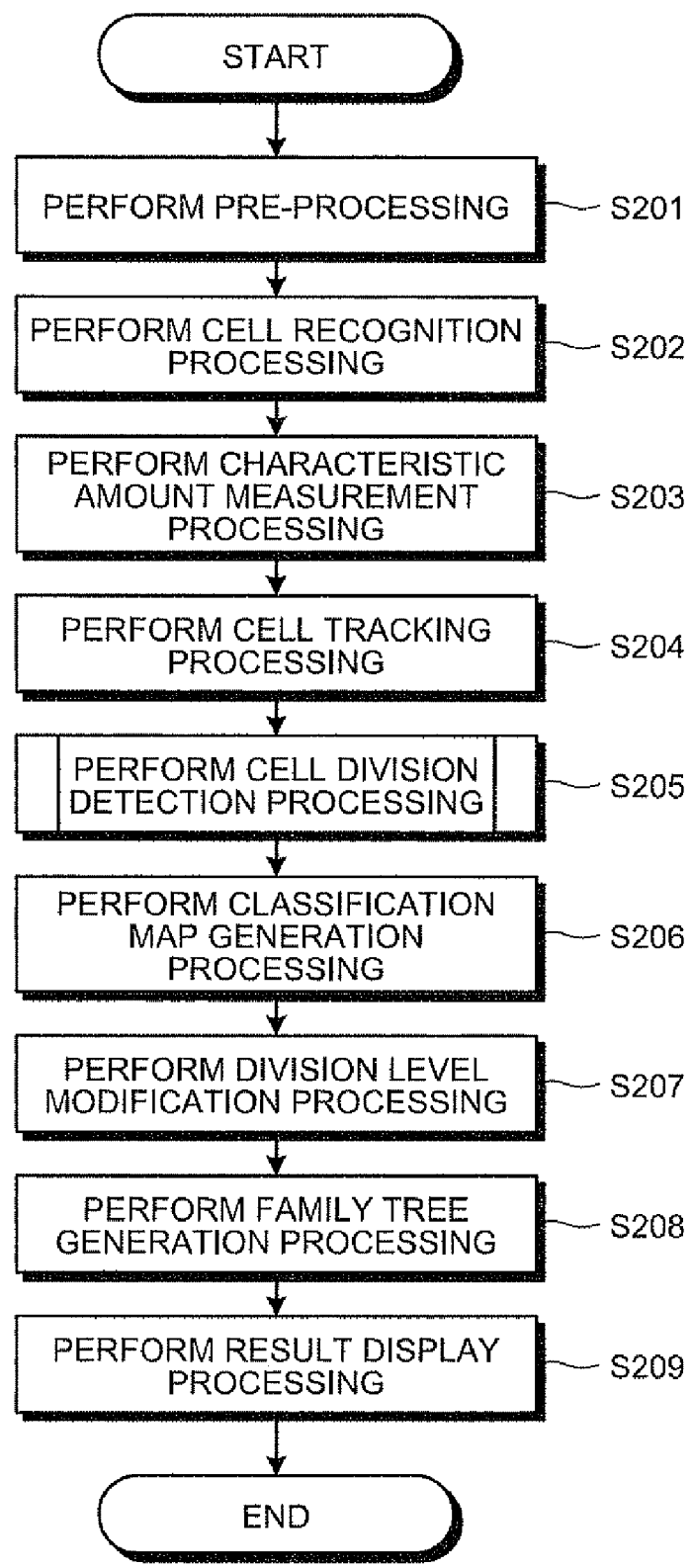
FIG. 17 is a flowchart of a process procedure performed by the image processing apparatus.

The process procedure performed by the image processing apparatus 11 is explained below. FIG. 17 is a flowchart of the process procedure performed by the image processing apparatus 11 for processing a series of observation images in response to execution of an image processing program by the control unit 16. At steps S201 to S205 shown in FIG. 17, processing is performed as at steps S101 to S105 shown in FIG. 3.

Figure 18:
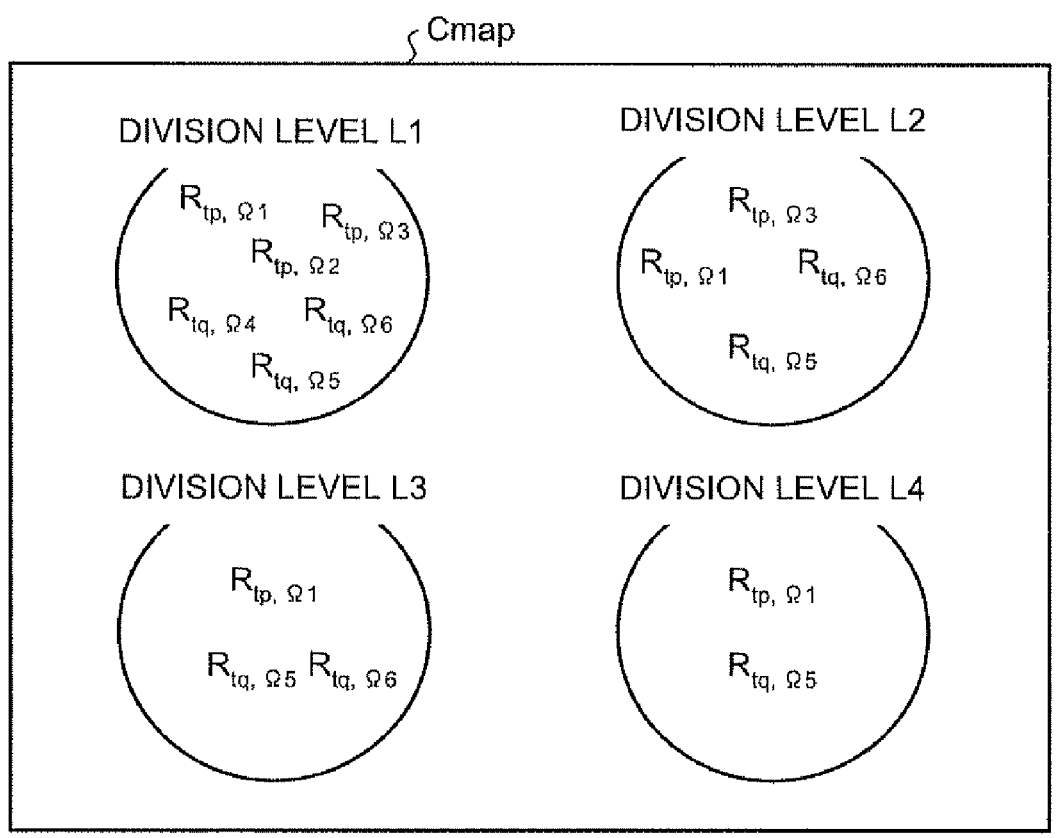
FIG. 18 is a diagram of an example of a division level classification map.

Thereafter, in the subsequent classification map generation processing at step S206, the classification map generation processing unit 12g classifies tracking labels of cell areas to the division labels $L_1$ to $L_4$ based on cell characteristic data of each cell area, and generates a division level classification map Cmap. For example, the tracking labels of the respective cell areas are divided into groups on based on each "division level $L_{num}$" ($1 \leq num \leq 4$) into which cell areas are sorted by the division detection processing unit 2e, and grouped tracking labels are displayed as character information as shown in FIG. 18. The groups classified based on a "division level $L_{num}$" basis is referred to as "class", and each class is identified by a class name with a division level name.

In division level modification processing at step S207, the image display control unit 16b outputs the division level classification map Cmap to the display unit 3 and causes the display unit 3 to display it, and the image processing control unit 16a waits until the division level modification instruction information is input thereto from the modification instruction input unit 14c. Meanwhile, the image display control unit 16b can generate display data based on the display item selection information entered by the observer or the like via the display item selecting unit 4b, and cause the display unit 3 to display the display data. Therefore, the observer or the like can cause the display unit 3 to display the display image, call characteristic data, and family tree information and the like of a desired cell area, and confirm them. The observer or the like can select a desired cell area on a cell area basis or a "division level $L_{num}$ class" ($1 \leq num \leq 4$) basis based on the display item selection information.

Thereafter, when the division level modification instruction information is input from the modification instruction input unit 14c, the division level modification processing unit 12h modifies and updates the cell characteristic data of the specified cell area based of the modification contents indicated by the division level modification instruction information. Specifically, for example, when division level modification instruction information for shifting a cell area $R_{tu},\Omega\xi$ classified to "division level L3 class" to "division level L4 class" is input, the division level modification processing unit 12h modifies the division label $L_3$ recorded in the cell characteristic data about the cell area $R_{tu},\Omega\xi$ to the division label $L_4$, and adds a parent-child label $GT_{(tu',\Omega\xi),(tu,\Omega\xi)}$ to the cell characteristic data about a parent cell area $R_{tu}',\Omega\xi$ corresponding to the cell area $R_{tu},\Omega\xi$. The parent cell area $R_{tu}',\Omega\xi$ is a cell area existing at an observation time point earlier than that at which the cell area $R_{tu},\Omega\xi$ exists and most close to an observation time point $t_u$ among the cell areas having the tracking label $\Omega\xi$. The variables u, u' and $\xi$ are integers.

When division modification instruction information for shifting a cell area classified to "division level L4 class" to "division level L3 class" is input, the division level modification processing unit 12h modifies the division label $L_4$ recorded in the cell characteristic data about the cell area to the division label $L_3$, and newly adds a cause label indicating that the label is modified to the cell characteristic data.

Using, for example, the mouse of the input unit 14, the observer or the like drags and drops a tracking label of a desired cell area to shift the tracking label to a different class on the division level classification map Cmap displayed on the display unit 3, thereby entering division modification instruction information.

In family tree generation processing at step S208, the family tree generation processing unit 2f generates family tree information based on the cell characteristic data, which is modified at step S207, as in the case of step S106. In result display processing at step S209, the image display control unit 16b generates display data and causes the display unit 3 to display the display data as in the case of step S107.

As explained above, in the image processing apparatus 11 according to the second embodiment, the assigned class of each cell area classified by the cell division detection processing can be changed based on the division level modification instruction information. In addition, based on the change, the cell characteristic data can be automatically modified and updated. This makes it possible to detect a division cell area in reflection of, for example, determination by the observer, which achieves more accurate detection of division cell areas.

Third Embodiment

Subsequently, a third embodiment of the present invention is explained. In the first and second embodiments, fluorescence images and phase contrast images are processed as observation images. In the third embodiment, processing is performed specializing in phase contrast images and similar types of images.

Figure 19:
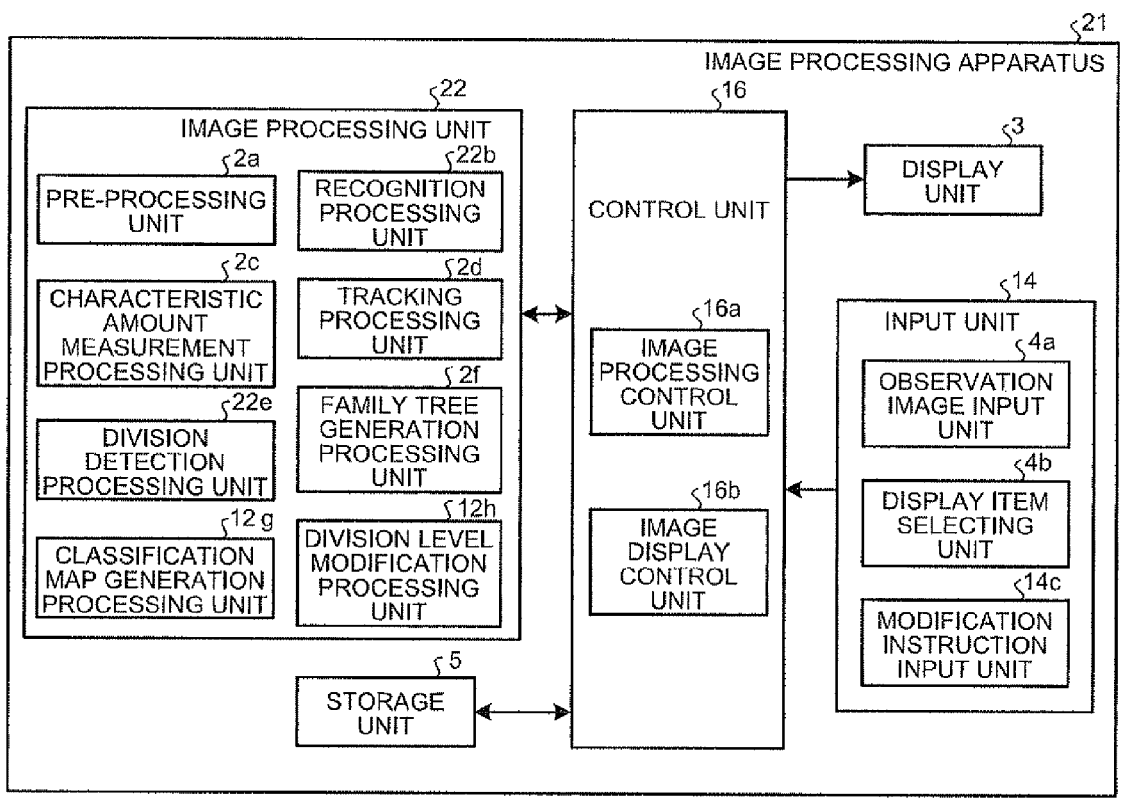
FIG. 19 is a block diagram of a configuration of an image processing apparatus according to a third embodiment of the present invention.

FIG. 19 is a block diagram of a configuration of an image processing apparatus 21 according to the third embodiment. As shown in FIG. 19, the image processing apparatus 21 has basically has the same configuration as that of the image processing apparatus 11, and includes an image processing unit 22 instead of the image processing unit 12. The image processing unit 22 basically has the same configuration as that of the image processing unit 12, and includes a recognition processing unit 22b and a division detection processing unit 22e instead of the recognition processing unit 2b and the division detection processing unit 2e. Other constituents are same as those of the second embodiment, and the same constituents are denoted by the same reference numerals.

As the image processing apparatus 11, the image processing apparatus 21 processes a series of observation images according to the process procedure shown in FIG. 17. However, because the image processing apparatus 21 processes phase contrast images or similar types of images processed as observation images, processing different from that performed by the image processing apparatus 11 is performed at the cell recognition processing (step S202) and the cell division detection processing (step S205), which is explained in detail below.

In the cell recognition processing, because a luminance value of an area in which a living cell exists is observed as a luminance value different from that of the background in an observation image, the recognition processing unit 22b recognizes the cell area by extracting pixels corresponding to the cell area based on a predetermined threshold. Specifically, first, the recognition processing unit 22b obtains a difference between a luminance of each pixel in the observation image with a luminance value $V_{back}$ of the representative background, and extracts only pixels each having the deference larger than a predetermined value Th_V. Specifically, using a luminance value $V_Q$ of a pixel Q in the observation image, the recognition processing unit 22b extracts the pixel Q as a pixel corresponding to the cell area when the following Equation (37) is satisfied.

$$V_Q - V_{back} > Th\_V \tag{37}$$

Thereafter, the recognition processing unit 22b performs known labeling processing on extracted pixels and integrating adjacent pixels, thereby recognizing the cell area.

Figure 20:
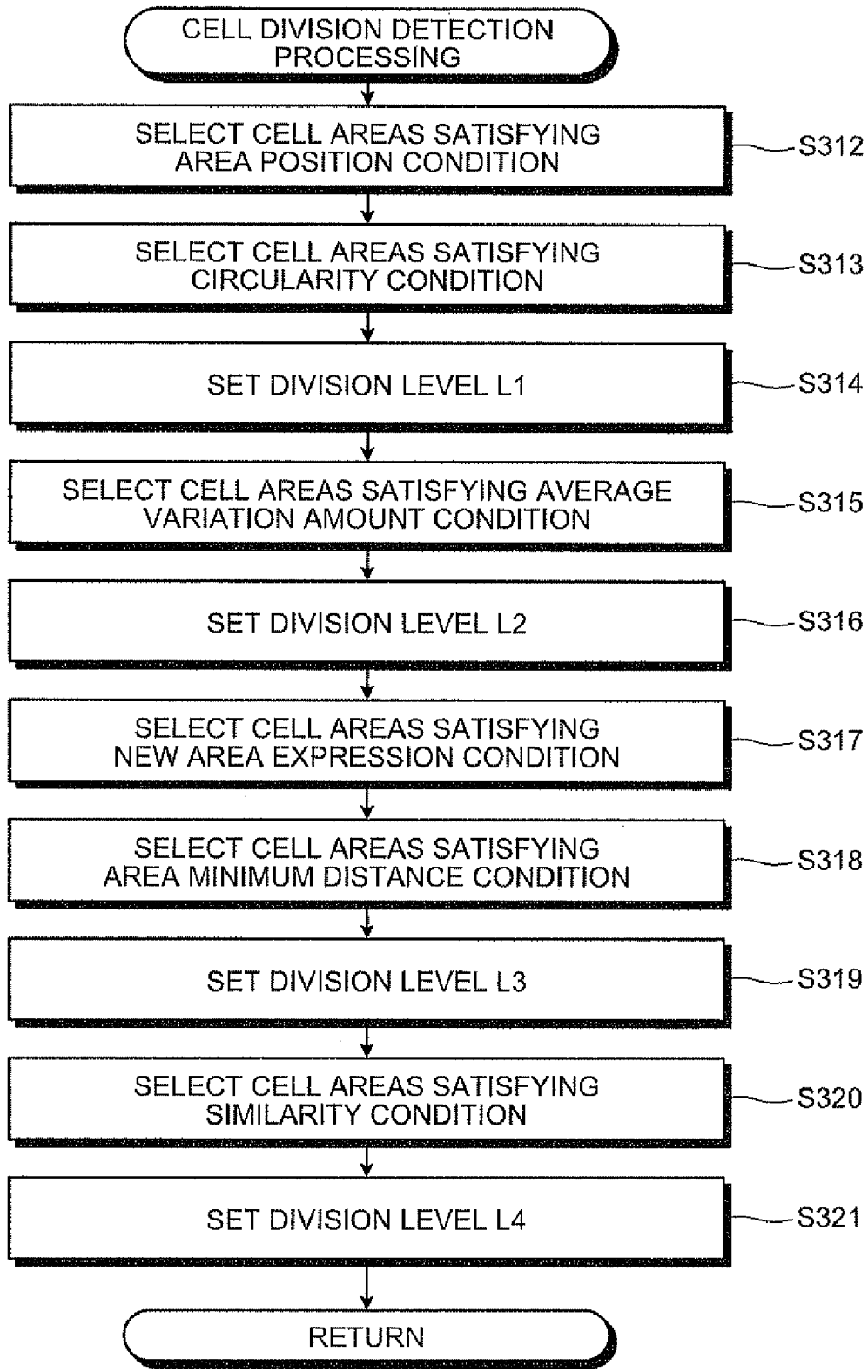
FIG. 20 is a flowchart of a process procedure of cell division detection processing.

In the cell division detection processing, basically following the procedure of the cell division detection processing of the first and second embodiment while omitting the determination processing based on luminance information about cell areas, the division detection processing unit 22e sorts the cell areas into "division level $L_{num}$" ($1 \leq num \leq 4$). FIG. 20 is a flowchart of the cell area processing procedure.

As shown in FIG. 20, omitting the processing for selecting cell areas based the total-luminance variation rate condition corresponding to step S201 shown in FIG. 6, the division detection processing unit 22e sorts cell areas highly likely to be division cell areas into "division level L1" by performing processing for selecting cell areas based on the area position condition and the circularity condition. Steps S312 to S314 shown in FIG. 20 are performed as steps S112 to S114 are performed.

Subsequently, at steps S315 and S316, basically following the processing at steps S115 and S116 while omitting the determination processing using the average luminance, average variation amount of average luminance, average of average luminance, and luminance information, the division detection processing unit 22e selects cell areas satisfying the average variation amount condition and sorts the selected cell areas into "division level L2".

Thereafter, the division detection processing unit 22e performs steps S317 and 319 as steps S117 and S119 is performed, thereby sorting cell areas satisfying the new area expression condition and the area minimum distance condition into "division level L3".

Finally, at steps S320 and 321, basically following steps S120 and S121, the division detection processing unit 22e selects cell areas satisfying the similarity condition using the similarity calculated without the average luminance, and sorts the selected cell areas into "division level L4" and detects the cell areas as division cell areas.

A phase contrast image has high contrast from which information about cell shape can be accurately obtained. Therefore, even when the division detection processing unit 22e performs the cell division detection processing without the luminance information as described above, the division detection processing unit 22e can accurately detect division cell areas. Furthermore, because the processing using the luminance information is omitted, the processing load is reduced, which achieves high-speed cell division detection processing.

The best modes for carrying out the present invention are explained as the fires to third embodiments above. However, the present invention is not limited to the first to third embodiments, and various modifications can be made within the scope of the present invention.

For example, in the first to third embodiments, the cell division detection processing is explained as one in which each of the division detection processing units 2e and 22e processes and selects all target cell areas on a determination condition basis and gradually narrows down the target cell areas based on the division levels. Alternatively, the series of determination conditions can be processed on a target cell area basis to sequentially sort the division cell areas into division levels.

As the pixel value explained in the first to third embodiments as one processed by the image processing apparatuses 1, 11, and 21, a luminance value, a density value, a gradation value, an intensity value, or the like is appropriately selected depending on the mode of an observation image. Furthermore, the luminance value explained as one processed by the image processing apparatuses 1, 11, and 21 can be understood by being appropriately replaced with a density value, a gradation value, an intensity value, or the like depending on the mode of an observation image.

The various type of labels explained as those added by the image processing units 2, 12, and 22 in the first to third embodiments can be arbitrarily expressed using numbers, alphabets, symbols as long as they are unique to each cell area.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus that processes a series of observation images captured at a plurality of time points, in which a living cell is chronologically recorded, the image processing apparatus comprising:
    a cell recognizing unit that recognizes cell image areas corresponding to the living cell from the series of observation images;
    a characteristic amount measuring unit that measures cell characteristic amounts that represent characteristics of each of the cell image areas;
    a cell tracking unit that determines whether a tracking target area captured at a processing target time point among the cell image areas has an identity with a cell image area captured at a time point earlier than the processing target time point among the cell image areas, and that adds a tracking index indicating the an identity to the tracking target area on which it is determined that the tracking target area has the an identity; and
    a cell division detecting unit that regards a cell image area to which the tracking index is added as a target cell area to be processed, measuring relative position information indicating a relative position relationship between the target cell area and a peripheral cell area positioned around the target cell area, determining whether cell division has occurred in the living cell represented by the target cell area based on at least the relative position information, and detecting the target cell area on which it is determined that cell division has occurred.

2. The image processing apparatus according to claim 1, wherein
    the cell tracking unit adds, to the tracking target area on which it is determined that the tracking target area does not have the an identity, a new tracking index indicating that the tracking target area has newly expressed, and
    the cell division detecting unit selects the cell image area to which the new tracking index is added, and measures the relative position information.

3. The image processing apparatus according to claim 1, wherein the cell division detecting unit determines whether cell division has occurred based on the relative position information, the cell characteristic amounts of the target cell area, and the cell characteristic amounts of an identical cell area to which the tracking index indicating an identity with the target cell area is added among the cell image areas.

4. The image processing apparatus according to claim 3, wherein the cell division detecting unit uses a tendency of variations in the cell characteristic amounts between the processing target time point and the time point earlier than the processing target time point to determine whether cell division has occurred.

5. The image processing apparatus according to claim 1, wherein the cell division detecting unit determines whether cell division has occurred based on a series of determination conditions based on at least the relative position information, and determines that cell division has occurred when the target cell area satisfies a determination condition at a predetermined level among the series of determination conditions.

6. The image processing apparatus according to claim 5, wherein the cell division detecting unit determines the level of the determination condition satisfied by the target cell area among the series of determination conditions, and adds a division level index indicating a level of possibility that cell division has occurred to the target cell area based on the level.

7. The image processing apparatus according to claim 6, further comprising:
    a level display control unit that causes a display unit to display the division level index;
    a modification instruction obtaining unit that obtains modification instruction information for modifying the division level index displayed on the display unit; and
    a division level modifying unit that modifies the division level index based on the modification instruction information.

8. The image processing apparatus according to claim 3, wherein the cell characteristic amounts include a position characteristic amount of the cell image area.

9. The image processing apparatus according to claim 3, wherein the cell characteristic amounts include a position characteristic amount of the cell image area and at least any one of a total luminance, a luminance average, an area, a circularity of the cell image area, and a variation amount of each of the characteristic amounts.

10. The image processing apparatus according to claim 1, wherein the cell division detecting unit measures a distance between the target cell area and the peripheral cell area as the relative position information.

11. The image processing apparatus according to claim 3, further comprising:
   a family tree generating unit that generates a family tree of the living cell, wherein
   the cell division detecting unit detects a daughter cell area that represents a daughter cell forming a pair with the living cell represented by the target cell area on which it is determined that cell division has occurred based on the relative position information, the cell characteristic amount of the target cell area, and the cell characteristic amount of the identical cell area, and
   the family tree generating unit generates a family tree of the living cell represented by the cell area on which it is determined that cell division has occurred based on a result of the detecting by the cell division detecting unit.

12. The image processing apparatus according to claim 11, further comprising a family tree display control unit that causes the display unit to display the family tree generated by the family tree generating unit as a tree diagram.

13. The image processing apparatus according to claim 1, further comprising a display control unit that causes the display unit 3 to display at least one of the cell image, the tracking index, the new tracking index, the cell characteristic amounts, the division level index, and the family tree.

14. A non-transitory computer program product having a computer readable medium including programmed instructions for processing a series of observation images captured at a plurality of time points, in which a cell area is chronologically recorded, wherein the instructions, when executed by a computer, cause the computer to perform:
   recognizing cell image areas corresponding to the living cell from the series of observation images;
   measuring cell characteristic amounts that represent characteristics of each of the cell image areas;
   determining whether a tracking target area captured at a processing target time point among the cell image areas has an identity with a cell image area captured at a time point earlier than the processing target time point among the cell image areas, and adding a tracking index indicating the an identity to the tracking target area on which it is determined that the tracking target area has the an identity; and
   regarding a cell image area to which the tracking index is added as a target cell area to be processed, measuring relative position information indicating a relative position relationship between the target cell and a peripheral cell area positioned around the target cell area, determining whether cell division has occurred in the living cell represented by the target cell area based on at least the relative position information, and detecting the target cell area on which it is determined that cell division has occurred.

* * * * *